US009212400B2

(12) United States Patent
van den Born et al.

(10) Patent No.: US 9,212,400 B2
(45) Date of Patent: Dec. 15, 2015

(54) TORQUE TENO VIRUS DIAGNOSTICS

(75) Inventors: Erwin van den Born, Wageningen (NL);
Vivian Cornelissen-Keijsers, Leunen (NL); Tuija Kekarainen, Barcelona (ES); Joaquim Segalés, Vic (ES); Laura Martinez-Guinó, Manresa (ES); Maria Ballester, Sabadell (ES)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/122,496

(22) PCT Filed: May 30, 2012

(86) PCT No.: PCT/EP2012/060109
§ 371 (c)(1),
(2), (4) Date: Nov. 26, 2013

(87) PCT Pub. No.: WO2012/163949
PCT Pub. Date: Dec. 6, 2012

(65) Prior Publication Data
US 2014/0248602 A1 Sep. 4, 2014

(30) Foreign Application Priority Data
May 31, 2011 (EP) ..................................... 11168280

(51) Int. Cl.
*C12Q 1/70* (2006.01)
(52) U.S. Cl.
CPC ..................................... *C12Q 1/701* (2013.01)
(58) Field of Classification Search
None
See application file for complete search history.

(56) References Cited

U.S. PATENT DOCUMENTS

2011/0045019 A1* 2/2011 Meng et al. ................. 424/204.1
2014/0248602 A1* 9/2014 van den Born et al. ........... 435/5

FOREIGN PATENT DOCUMENTS

WO 2010/044889 A2 4/2010
WO 2011/031438 A2 3/2011

OTHER PUBLICATIONS

Sequence alignment of instant SEQ ID No. 1 with geneseq database access No. AZF42441 submitted as SEQ ID No. 39 Mar. 31, 2011 by Meng et al.*
Sequence alignment of instant SEQ ID No. 2 with geneseq database access No. AZF42444 submitted as SEQ ID No. 42 Mar. 31, 2011 by Meng et al.*
Sequence alignment of instant SEQ ID No. 3 with Geneseq database acc No. AZF42413 submitted as SEQ ID No. 11 Mar. 2011 by Meng et al.*
Gallei et al. (Veterinary Microbiology. 2010; 143: 202-212).*
Sequence alignment of SEQ ID No. 4 with geneseq database access No. AZF42413 submitted as SEQ ID No. 11 Mar. 31, 2011 by Meng et al.*
Sequence alignment of SEQ ID No. 5 with geneseq database access No. AZF42413 submitted as SEQ ID No. 5 Mar. 31, 2011 by Meng et al.*
Sequence alignment of SEQ ID No. 6 with geneseq database access No. AZQ26232 submitted as SEQ ID No. 15 Dec. 8, 2011 by Ni et al.*
Sequence alignment of SEQ ID No. 7 with geneseq database access No. ANN54149 submitted as SEQ ID No. 7 Jan. 24, 2008 by Ishii et al.*
Sequence alignment of SEQ ID No. 8 with geneseq database access No. ANN54148 submitted as SEQ ID No. 6 Jan. 24, 2008 by Ishii et al.*
Hoffmann et al. Journal of Virological Methods. 206; 136: 200-209).*
Brassard, et al., "Development of a real-time TaqMan PCR assay for the detection of porcine and bovine Torque teno virus", Journal of Applied Microbiology, 2009, pp. 2191-2198, vol. 108.
Gallei, et al., "Porcine Torque teno virus: Determination of viral genomic loads by genogroup-specific multiplex rt-PCR, detection of frequent multiple infections with genogroups 1 or 2, and establishment of viral full-length sequences", Veterinary Microbiology, 2010, pp. 202-212, vol. 143.
Savic, et al., "Detection rates of the swine torque teno viruses (TTVs), porcine circovirus type 2 (PCV2) and hepatitis E virus (HEV) in the livers of pigs with hepatitis", Veterinary Research Communications, 2010, pp. 641-648, vol. 34.
European Search Report for EP Application No. EP 11 16 8280, dated Oct. 12, 2011.
PCT International Search Report for corresponding PCT/EP2012/060109, mailed on Sep. 7, 2012.

* cited by examiner

*Primary Examiner* — Shannon A Foley

(57) ABSTRACT

The present invention relates to methods for the detection of the presence of swine Torque Teno virus in a sample, for the detection of replication of swine Torque Teno virus in a sample, to Torque Teno virus (RT)-PCR primers and probes, and to diagnostic test kits for the detection of the presence and replication of swine Torque Teno virus in a sample.

11 Claims, 9 Drawing Sheets

Figure 1A:
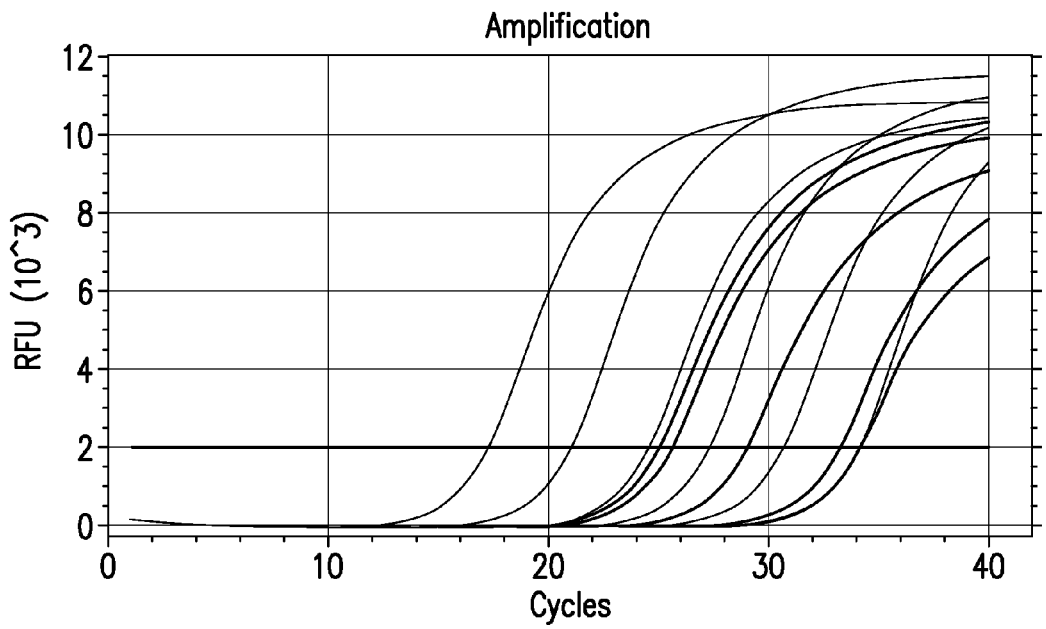

ADDENDUM 1
Plasmid TTV008:

Plasmid TTV008 comprises a 323 bp fragment, generated by amplification from DNA isolated of Hyclone (FSD29672) porcine serum using the primers TTV2-106F (AGTTACACATAACCACCAAACC) and TTV2-425R (GCAGTACGCTACCGTCAGCCATC), was cloned in the vector pSC-A-amp/kan following the instruction manual of the StrataClone PCR cloning kit (Stratagene).

TTV008 Sequence of the insert:
AGTTACACATAACCACCAAACCACAGGTAAACTCTGCAAAAAAGAGGAAATAAATCTCATTG
GTTGGGCCAGAAGTCCTCATTAGAATACTAAAAGGACCAATCAGAAACACTTCCTCTTTTAGA
GTATATAAGTAAGTGCGCAGACGAATGGCTGAGTTTATGCCGCTGGTGGTAGACACGAACAG
AGCTGAGTGTCTAACCGCCTGGGCGGGTGCCGGAGCTCCTGAGAGCGGAGTCAAGGGGCCTA
TCGGGCAGGCGGTAATCCAGCGGAACCGGGCCCCCCCCTCAATGGAAGAAAGATGGCTGACG
GTAGCGTACTGC

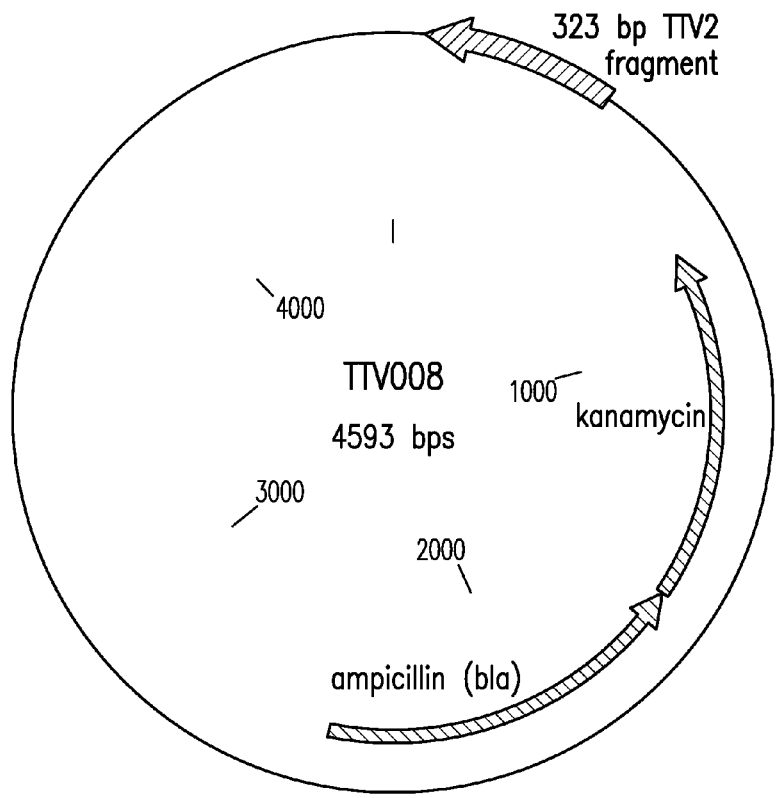

| | 380 | 390 | 400 | 410 | 420 | 430 | 440 | 450 |
|---|---|---|---|---|---|---|---|---|
| TTV2_(AY823990)/1-2735 | GCCTGGGCGGGTGCCGGAGC | ------- | TCCTGAGAGCGGAGTCGAGTCAAGGGGCCTATCGGGCAGGCGGTAATCCAGCGGAA |
| TTV2_(GE1)/1-2742 | GCCTGGGCGGGTGCCGGAGC | ------- | TCCTGAGAGCGGAGTCGAGTCAAGGGGCCTATCGGGCAGGCGGTAATCCAGCGGAA |
| TTV2_(GE9)/1-2742 | GCCTGGGCGGGTGCCGGAGC | ------- | TCCTGAGAGCGGAGTCGAGTCAAGGGGCCTATCGGGCAGGCGGTAATCCAGCGGAA |
| TTV2_(G31)/1-2744 | GCCTGGGCGGGTGCCGGAGC | ------- | CCCTGAGAGCGGAGTCGAGTCAAGGGGCCTACCGGGCAGGCGGTAATCCAGCGGAA |
| TTV2_(G33)/1-2744 | GCCTGGGCGGGTGCCGGAGC | ------- | TCCTGAGAGCGGAGTCGAGTCAAGGGGCCTATCGGGCAGGCGGTAATCCAGCGGAA |
| TTV2_(G43)/1-2736 | GCCTGGGCGGGTGCCGGAGC | ------- | TCCTGAGAGCGGAGTCGAGTCAAGGGGCCTATCGGGCAGGCGGTAATCCAGCGGAA |
| TTV2_(G61)/1-2736 | GCCTGGGCGGGTGCCGGAGC | ------- | TCCTGAGAGCGGAGTCGAGTCAAGGGGCCTATCGGGCAGGCGGTAATCCAGCGGAA |
| TTV2_(G64)/1-2745 | GCCTGGGCGGGTGCCGGAGC | ------- | TCCTGAGAGCGGAGTCGAGTCAAGGGGCCTATCGGGCAGGCGGTAATCCAGCGGAA |
| TTV2_(1907)/1-2744 | GCCTGGGCGGGTGCCGGAGC | ------- | TCCTGAGAGCGGAGTCGAGTCAAGGGGCCTATCGGGCAGGCGGTAA-CCTGCGGAA |
| TTV2_(HM633240)/1-2822 | GCCTGGGCGGGTGCCGGAGC | ------- | TCCTGAGAGCGGAGTCGAGTCAAGGGGCCTTATCGGGCAGGCGGTAATCCAGCGGAA |
| TTV2_(HM633224.1)/1-2803 | GCCTGGGCGGGTGCCGGAGC | ------- | TCCTGAGAGCGGAGTCGAGTCAAGGGGCCTATCGGGCAGGCGGTAATCCAGCGGAA |
| TTV2_(HM633215.1)/1-2807 | GCCTGGGCGGGTGCCGGAGC | ------- | TCCTGAGAGCGGAGTCGAGTCAAGGCCCCTATCGGGCAGGCGGTAATCCAGCGGAA |
| TTV2_(HM633216.1)/1-2807 | GCCTGGGCGGGTGCCGGAGC | ------- | TCCTGAGAGCGGAGTCGAGTCAAGGGGCCTATCGGGCAGGCGGTAATCCAGCGGAA |
| TTV2_(HM633217.1)/1-2796 | GCCTGGGCGGGTGCCGGAGC | ------- | TCCTGAGAGCGGAGTCGAGTCAAGGGGCCTATCGGGCAGGCGGTAATCCAGCGGAA |
| TTV2_(HM633218.1)/1-2803 | GCCTGGGCGGGTGCCGGAGC | ------- | TCCTGAGAGCGGAGTCGAGTCAAGGGGCCTATCGGGCAGGCGGTAATCCAGCGGAA |
| TTV2_(HM633219.1)/1-2809 | GCCTGGGCGGGTGCCGGAGC | ------- | TCCTGAGAGCGGAGTCGAGTCAAGGGGCCTATCGGGCAGGCGGTAATCCAGCGGAA |
| TTV2_(HM633226.1)/1-2824 | GCCTGGGCGGGTGCCGGAGC | ------- | TCCAGAGAGCGGAGTCGAGTCAAGGGGGACCTATCGGGCAGGCGGTAA-CCTGCGGAA |
| TTV2_(HM633227.1)/1-2802 | GCCTGGGCGGGTGCCGGAGC | ------- | TCCTGAGAGCGGAGTCGAGTCAAGGGGCCTATCGGGCAGGCGGTAATCCAGCGGAA |
| TTV2_(HM633228.1)/1-2796 | GCCTGGGCGGGTGCCGGAGC | ------- | TCCTGAGAGCGGAGTCGAGTCAAGGGGCCTATCGGGCAGGCGGTAATCCAGCGGAA |
| TTV2_(HM633220.1)/1-2805 | GCCTGGGCGGGTGCCGGAGC | ------- | TCCTGAGAGCGGAGTCGAGTCAAGGGGCCTATCGGGCAGGCGGTAATCCAGCGGAA |
| TTV2_(HM633229.1)/1-2834 | GCCTGGGCGGGTGCCGGAA | ------- | TCCAGAGAGCGGAGTCGAGTCAAGGGGCCTATCGGGCGGGCGGTAA-CCTGCGGAA |

TORQUE TENO VIRUS DIAGNOSTICS

CROSS-REFERENCE TO RELATED APPLICATIONS

This application is a national stage entry under 35 U.S.C. §371 of PCT/EP2012/060109, filed on May 30, 2012, which claims priority to EP Application No. 11168280.3, filed on May 31, 2011. The content of PCT/EP2012/060109 is hereby incorporated by reference in its entirety.

The present invention relates to a method for the detection of the presence of swine Torque Teno virus in a sample, for the detection of replication of swine Torque Teno virus in a sample, to Torque Teno virus (RT)-PCR primers and probes, and to diagnostic test kits for the detection of the presence and replication of swine Torque Teno virus in a sample.

Torque Teno viruses (TTV's) are small, non-enveloped viruses with a circular negative-sense single-stranded DNA (ssDNA) genome. They belong to the family Anelloviridae.

The first TTV was characterised in 1997 by Nishizawa T, et al. The virus was identified in the blood of a patient who suffered from post-transfusion hepatitis and presented with abnormal liver enzymes levels but no classic hepatitis viruses. TTV was later detected in many non-human species such as non-human primates, cats, dogs, tupaias and swine (Leary et al., 1999, Martinez et al., 2006).

Torque teno sus virus 1 (TTSuV1) and Torque teno sus virus 2 (TTSuV2), both infecting domestic pig and wild boar (and thus also referred to as swine TTV's, or briefly sTTV's) are classified as belonging to the Iotatorquevirus genus. It is believed that TTV's might influence the development of some diseases or even modulate the outcome of disease by being present in blood or tissues (Okamoto, 2009).

A clear-cut pathogenic role of TTV's has not been demonstrated to date and its role during co-infection with other pathogens is under debate, especially with regard to porcine Circovirus diseases (PCVDs) (Kekarainen et al., 2006, Ellis et al., 2008, Taira et al., 2009).

TTV's share conserved genomic regions and conserved functions with economically important circular ssDNA viruses of swine and poultry namely, Porcine circovirus-2 (PCV2) and Chicken anemia virus (CAV), both members of the Circoviridae family. sTTV's have a genomic organization that is similar to TTV's that infect humans, but they share less than 45% nucleotide sequence identity (Niel et al., 2005; Okamoto et al., 2002). Recent studies also demonstrated a high degree of genetic variability between various sTTV's such as sTTV1 and sTTV2 (Huang et al., 2010, Cortey et al., 2010). The genome of sTTV is approximately 2.8 kbp in length and two major potential protein-coding genes, open reading frame (ORF) 1 and ORF2, can be deduced from the nucleotide sequence. By analogy with related ssDNA viruses, ORF 1 is believed to encode the viral capsid protein. ORF2 encodes a non-structural protein, assumed to be involved in viral replication (Hijikata et al., 1999; Huang et al., 2010). TTV ORF2 has been also associated with the NF78 KB pathway suppression (Zheng at al., 2007). Analysis of sTTV nucleotide sequence reveals the existence of an additional ORF, ORF3, generated by RNA splicing and shares its 5' end with ORF2. ORF3 is believed to encode a non-structural protein with unknown function (Okamoto et al., 2000; Biagini et al., 2001).

Research on anelloviruses has been based almost solely on PCR techniques. Recently, tissue culture systems allegedly supporting human TTV replication, albeit with an inefficient propagation, have been reported (Kakkola et al., 2007; Leppik et al., 2007). However, for sTTV, no tissue culture systems supporting sTTV growth and replication are know.

The impossibility to grow sTTV in vitro has severely hampered sTTV research. For that reason, to date, studies have mainly focused on molecular virology, transcription and expression strategies of different human TTV genotypes. Three mRNAs were produced after transfection with a plasmid containing TTV genotype 1 genome driven by a putative promoter in COS-1 cells (Kamahora et al., 2000). Moreover, after alternative splicing and alternative translation processes six different proteins from genotype 6 and seven different proteins from isolate P/1C1 (genotype 1) have been described (Qiu at al., 2005; Mueller et al., 2008). Additional splicing events and intragenomic rearrangements of TTV's were identified in lymphoma-derived and T-cell leukemia cell lines (Leppik et al., 2007).

There are only few studies on human TTV protein localization and results are fairly contradictory. TTV genotype 6 ORF1 and ORF2 proteins were localized in the cytoplasm of transfected cells (Qiu et al., 2005). On the contrary, in a more recent study, ORF1 protein was located in the nucleus (specifically, within the nucleoli), while the ORF3 was observed in the nucleus but not in a nucleolus. In the same study, the ORF2 protein was found, as described previously, in the cytoplasm (Mueller at al., 2008). Discrepancies observed between studies suggest that the genomic diversity found in TTV isolates can be associated with different strategies of expression and localization of viral proteins (Mueller et al., 2008).

It has been suggested that the transcriptional profile of sTTV could be similar to that found in human TTV's (Okamoto et al., 2002), but experimental evidence is still lacking.

Due to the impossibility to propagate sTTV in cell culture, sTTV detection and diagnosis are currently based on conventional polymerase chain reaction (PCR) methods. Especially for the detection of ssDNA viruses like TTV's that have extremely variable genomes even within subgroups infecting the same specific host or host group, the choice of appropriate PCR primer binding sites and, if desired, probe binding sites is crucial.

A general problem of PCR primers for sTTV detection is that, although they may have a high specificity for sTTV strains of the same geographical origin and the same genotype, they may possibly not react with sTTV strains of a different geographical origin or another genotype. As a consequence, the presence of some sTTV strains in swine herds as well as in biological material may remain unnoticed.

It is clear that reliable and universal diagnostic tools for the detection of sTTV in swine herds are essential, if only to detect the presence or absence of sTTV in an animal.

Such tools would also be essential to monitor the geographical spreading of sTTV. This could i.a. reveal the presence or absence of sTTV strains from a certain geographical origin or a certain genotype in swine on a different geographical location.

There is also a need for reliable diagnostic tools in the field of vaccine production. Many of the swine virus vaccines (and not only swine vaccines) are produced in cell cultures. Certain cell culture media components and cell lines are of swine origin. So it is important to check for the absence of sTTV in these cell cultures and in vaccines produced using these cell cultures.

An even greater need exists for quantitative methods and diagnostic tools that are able to give an indication of not only the presence, but also the amount of sTTV in various types of sample material. This would i.a. greatly facilitate studies on the pathology of sTTV.

And most importantly, sTTV could be present in tissue with or without replicating there. It is known that TTV is found in practically all tissues and organs, but it is not known if it is merely found there because it was transported to that tissue by the blood or if it is actively replicating there.

Therefore, a test that could discriminate between the mere presence of sTTV in e.g. a tissue and active replication of the virus in that tissue is highly needed. Such a test would additionally make it possible to detect if traces of sTTV in cell culture are or aren't in a non-replicating form. This would make sTTV vaccine production in cell culture even more safe.

Thus there is a clear need for reliable methods and diagnostic tools that are able to detect sTTV strains irrespective of the geographical origin and the genotype of those sTTV strains. And moreover, there is a need for reliable methods and diagnostic tools that are able to detect viral replication activity of such sTTV strains.

It is an objective of the present invention to provide such methods and diagnostic tools.

Surprisingly now specific primer sets have been found that, if desired in combination with a specific probe, are capable of detecting the presence or absence of sTTV strains, irrespective of the geographical origin or the genotype of those TTV strains.

In a method according to the invention, the detection of TTV in a sample can now be done by performing the following method steps:

a) performing a polymerase chain reaction (PCR) of said sample using a primer set comprising a forward primer that binds to a stretch of at least 14 consecutive nucleotides of an oligonucleotide FDNA-TTV having a sequence as depicted in SEQ ID NO.: 1, and a reverse primer that binds to a stretch of at least 14 consecutive nucleotides of an oligonucleotide RDNA-TTV-r1 having a sequence as depicted in SEQ ID NO.: 2 or a reverse primer that binds to a stretch of at least 14 consecutive nucleotides of an oligonucleotide RDNA-TTV-r2 having a sequence as depicted in SEQ ID NO.: 3 and
b) examining the PCR amplification result of step (a)

The term "primer" is used to describe an oligonucleotide that is capable to recognise, and to bind to, a complementary polynucleotide and to act as an initiation point for nucleic acid synthesis or replication along a complementary strand.

The term "capable to bind to a complementary polynucleotide" means capable of forming, under hybridisation conditions, a duplex structure with that polynucleotide The term "probe" refers to an oligonucleotide that is complementary to a polynucleotide of interest, and capable of forming, under hybridisation conditions, a duplex structure with that polynucleotide.

The word "probe" basically has the characteristics of a primer polynucleotide that additionally carries a specific marker. Such a marker can i.a. be a fluorophore, such as the fluorophores used in e.g. the TaqMan probes (vide infra).

The term "oligonucleotide" is used herein to describe a short polymer of nucleic acids. Such short polymer would usually have a length of between 10 and 100 nucleic acids.

The term "hybridisation conditions" relates to conditions that allow the primer or probe to anneal to the polynucleotide of interest. These conditions depend on the temperature and the ionic strength of the solution in which hybridisation is to take place. Hybridization reactions and conditions are well-known in the art and are i.a. described in the standard laboratory manual by Maniatis/Sambrook (34).

For the determination of hybridisation conditions, basically the following formulae are used: for the basic Melting Temperature (Tm) calculation for sequences longer than 13 nucleotides, the following equation can be used:

$$Tm=64.9+41*(yG+zC-16.4)/(wA+xT+yG+zC)$$

where w, x, y and z are the number of the bases A, T, G and C in the sequence, respectively (from Marmur, J., and Doty, P. (1962) *J Mol Biol* 5:109-118)

Additional information is given in: Wallace, R. B., Shaffer, J., Murphy, R. F., Bonner, J., Hirose, T., and Itakura, K. (1979) Nucleic Acids Res 6:3543-3557 and Sambrook, J., and Russell, D. W. (2001) Molecular Cloning: A Laboratory Manual. Cold Spring Harbor Laboratory Press; Cold Spring Harbor, N.Y.

The equation assumes that the annealing occurs under the standard conditions of 50 nM primer, 50 mM $Na^+$, and pH 7.0

For the basic salt adjusted Melting Temperature (Tm) calculation, the following equation can be used:

$$Tm=100.5+(41*(yG+zC)/(wA+xT+yG+zC))-(820/(wA+xT+yG+zC))+16.6*\log_{10}([Na^+])$$

where w, x, y and z are the number of the bases A, T, G and C in the sequence, respectively.

The term $16.6*\log_{10}([Na^+])$ adjusts the Tm for changes in the salt concentration. (Additional info is given in: Howley, P. M; Israel, M. F.; Law, M-F.; and M. A. Martin "A rapid method for detecting and mapping homology between heterologous DNAs. Evaluation of polyomavirus genomes." *J. Biol. Chem.* 254, 4876-4883, 1979).

PCR-techniques are equally well-known in the art and they are further extensively described in standard laboratory manuals such as; "Real-Time PCR: Current Technology and Applications", in "PCR primers, a laboratory manual", and in Maniatis/Sambrook (see references in literature list below).

The skilled artisan does realise that a primer or a probe doesn't need to be fully complementary to the polynucleotide of interest, as long as the hybridisation conditions are such that annealing can take place in spite of the incomplete complementarities.

In principle, a mismatch of one or more nucleotides can be compensated by lowering the Tm or by altering the salt concentration e.g. using the equations given above or the ample information in the literature cited above.

It should be realised that the use of a primer having a mismatch, usually necessitates the use of less stringent hybridisation conditions. And this in turn may sometimes lead to a lesser specificity. This needs not necessarily be a problem, given the small size of the TTV-genome. The chances of a primer having a mismatch binding to a non-specific TTV-sequence are very small.

Nevertheless, it is clear that primers that comprise a 100% complementarity match to a stretch of at least 14 consecutive nucleotides of an oligonucleotide having a sequence as depicted in SEQ ID NO.: 1, 2 or 3 are preferred.

The primers and the probe according to the invention can inter alia be used for the detection of sTTV in an animal or a sample of that animal.

The term "sample" is used herein to refer to any biological material that is suspected of containing sTTV. The biological material can i.a. be tissue such as swine liver, spleen, bone or muscle tissue, but it can also be a body fluid such as e.g. blood, urine, faecal material, amniotic fluid. The material can also be a cloacal, oral or nasal cavity swab or e.g. disrupted cells.

It goes without saying that the material to be tested can also be of non-porcine origin. It may well be that non-porcine species are suspected of carrying sTTV, or are tested in order to exclude that they carry sTTV.

A polymerase chain reaction, further referred to as PCR comprises the steps of heating a DNA molecule, in the presence of a primer set, to a temperature above the melting temperature, followed by cooling in order to allow the primers of the primer set to bind to the respective complementary DNA strands. The DNA-primer complexes form the starting points for the synthesis of a complementary DNA strand using the enzyme DNA polymerase in the presence of the four DNA building blocks A, T, G and C in the form of deoxynucleotide triphosphates (dNTPs). With these building-blocks the DNA polymerase synthesizes a new DNA strand.

Depending on the amount of sTTV-DNA in the sample (provided that it is present), several PCR-cycles will have to be performed before there is sufficient material to be detected. An average of between 30 and 45 cycles would not be unusual. The skilled artisan would be able, on the basis of the sequences of the primers and the probe, to determine the optimal temperature conditions for the various steps of the PCR-cycle using e.g. the formulae given above or in the standard laboratory manuals. (vide supra).

The term "a primer binding to a stretch of at least 14 consecutive nucleotides of an oligonucleotide having a sequence as depicted in SEQ ID NO.:" means that the primer should at least have the length of a stretch of at least 14 consecutive nucleotides that bind to the oligonucleotide as depicted in that SEQ ID NO.

Merely as an example: FDNA-TTV could have the sequence cgaatggctgagtttatgccgc as depicted in SEQ ID NO.: 1. Thus, a "primer binding to a stretch of at least 14 consecutive nucleotides of an oligonucleotide having a sequence as depicted in SEQ ID NO.: 1" should at least consist of a stretch of at least 14 consecutive nucleotides from the nucleotides cgaatggctgagtttatgccgc in that order. It could however be a longer primer that e.g. comprises the nucleotides cgaatggctgagtttatgccgc, and has one or more additional nucleotides at the 5'-end and/or the 3'-end.

The same is true for the probe (although it is clear that the probe should not have a length at which the quenching molecule is no longer quenching the fluorophore; vide infra). The oligonucleotide as depicted in SEQ ID NO.: 2 has a length of 17 nucleic acids, but again, the oligonucleotide of a primer or probe according to the invention should have a minimal length of at least 14 consecutive nucleotides binding to an oligonucleotide having a sequence as depicted in SEQ ID NO.: 2.

If a primer (or probe) is chosen that has additional nucleotides at the 5'-end and/or the 3'-end, such nucleotides may or may not be complementary to the 3'- and/or 5'-flanking regions of the complementary strand to which the primer binds. In some cases, the temperatures of the various RT-PCR cycles should possibly be adapted to the increased length of the primer and to the fact that one or more of the additional nucleotides are complementary. And again; the skilled artisan would be able, on the basis of the sequences of the primers and the probe, to determine the optimal temperature conditions for the various steps of the PCR-cycle using e.g. the formulae given above or in PCR text books referred to herein (vide supra).

Primers binding to a stretch 15, 16, 17, 18, 19 or even 20 or more consecutive nucleotides of an oligonucleotide having a sequence as depicted in SEQ ID NO.: 1-8 (with a max of 17 for SEQ ID NO: 2) are preferred in this order of preference, since they anneal even more selectively to sTTV-sequences.

Probes binding to a stretch 15, 16, 17, 18, 19, 20 or more consecutive nucleotides of an oligonucleotide having a sequence as depicted in SEQ ID NO.: 2 and 5 (with a max of 17 for SEQ ID NO: 2) are preferred in this order of preference, since they also anneal even more selectively to sTTV-sequences.

In principle, after step a) of the method of the present invention, there are now different ways to perform step b). The PCR step results in a PCR product of which the length and amount can be examined e.g. by means of conventional agarose or polyacrylamide gel electrophoresis. In case there is sTTV DNA present in the sample, the primer pair would anneal and therefore, after step a), a PCR product of the expected length would be detected on gel. If there is no sTTV DNA present in the sample, the primer pair, or at least one of the primers, would fail to anneal and therefore, no PCR product of the expected length would be detected.

As will be noticed, the oligonucleotides presented in SEQ ID NO: 1, 2, 3, 4 and 5 reflect the (few) differences in the sequences of the individual viruses in these regions. Possible consequences for the development of primers are discussed below (vide infra).

Figure 4A:
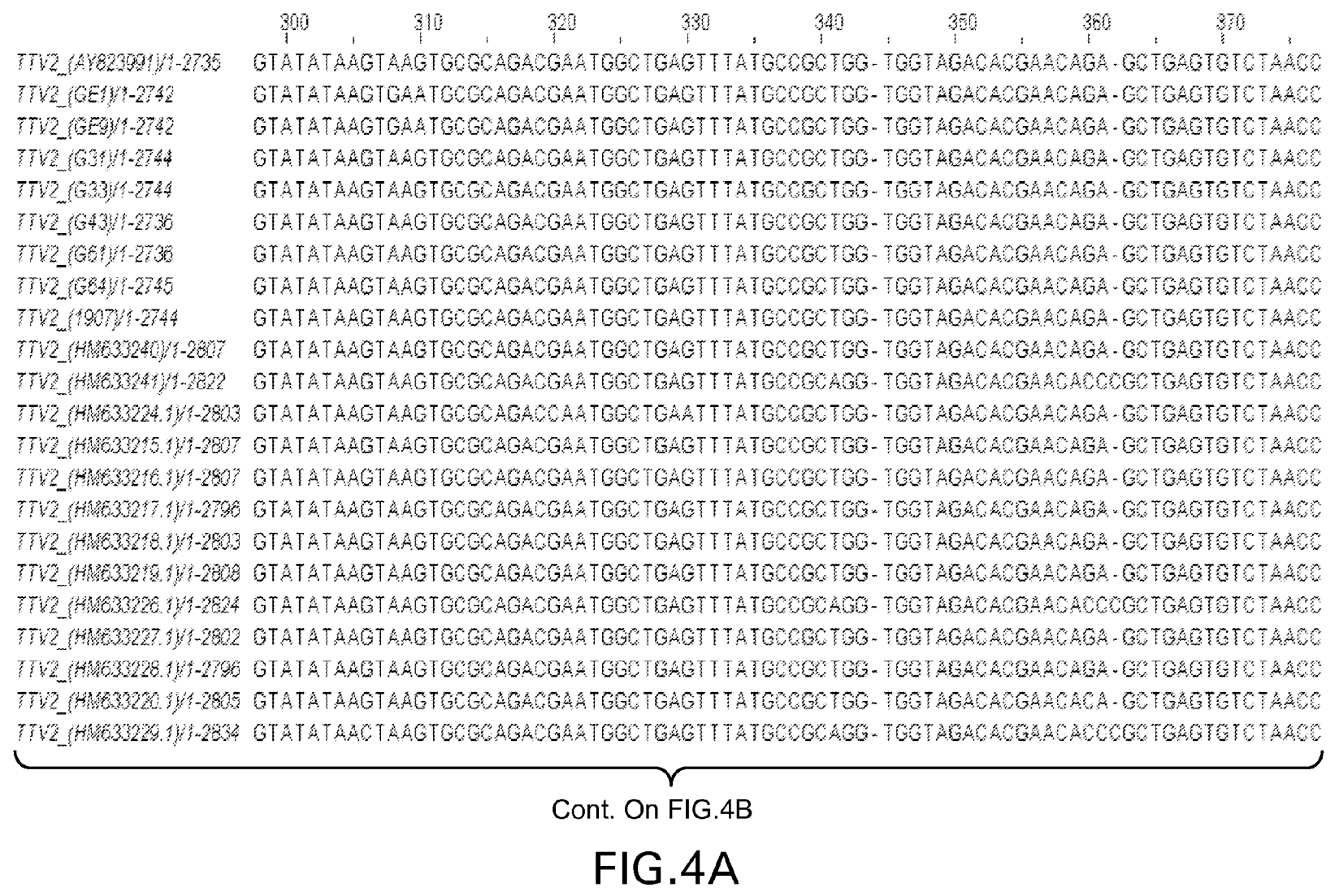
Figure 4B:
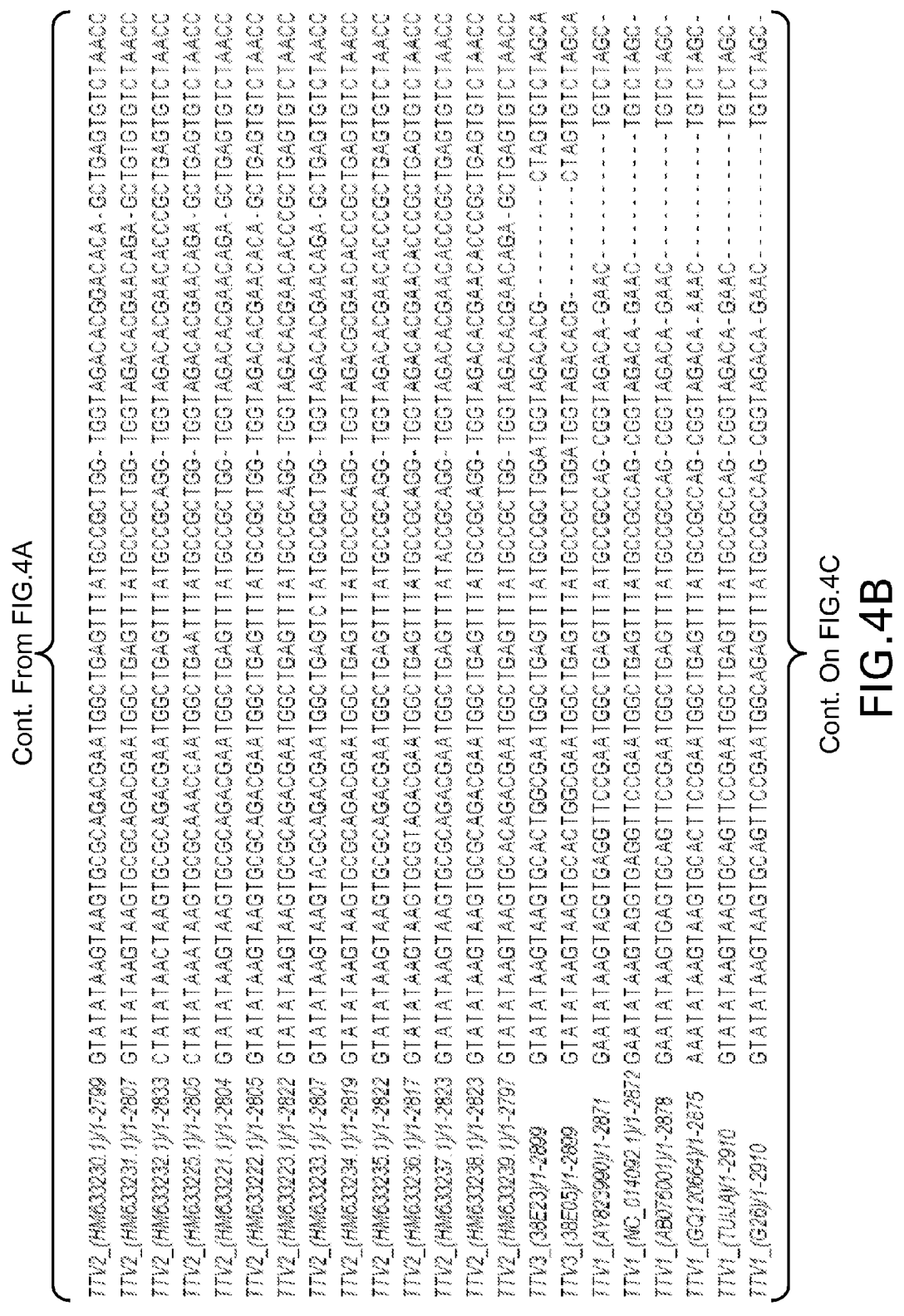
Figure 4C:
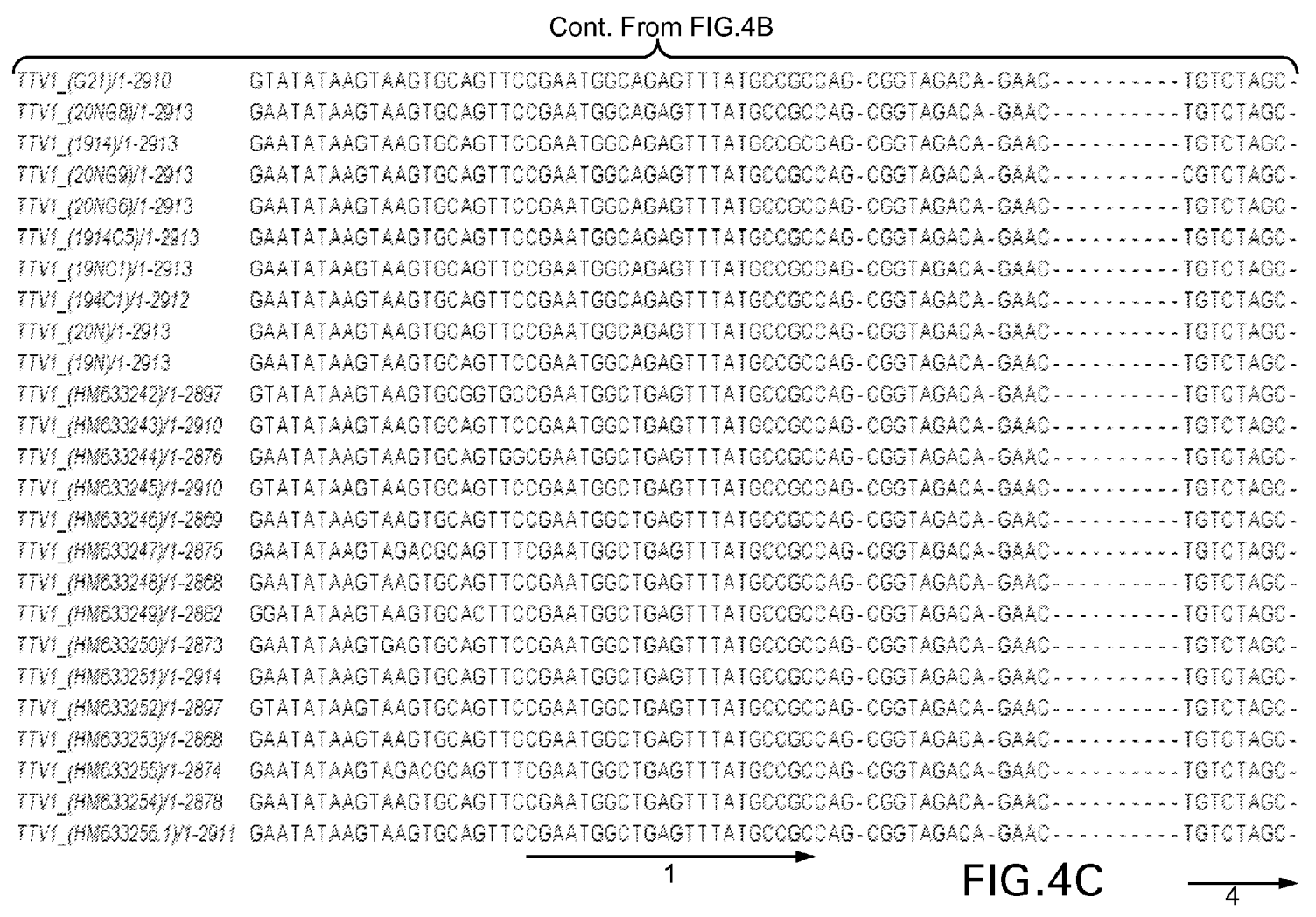
Figure 4E:
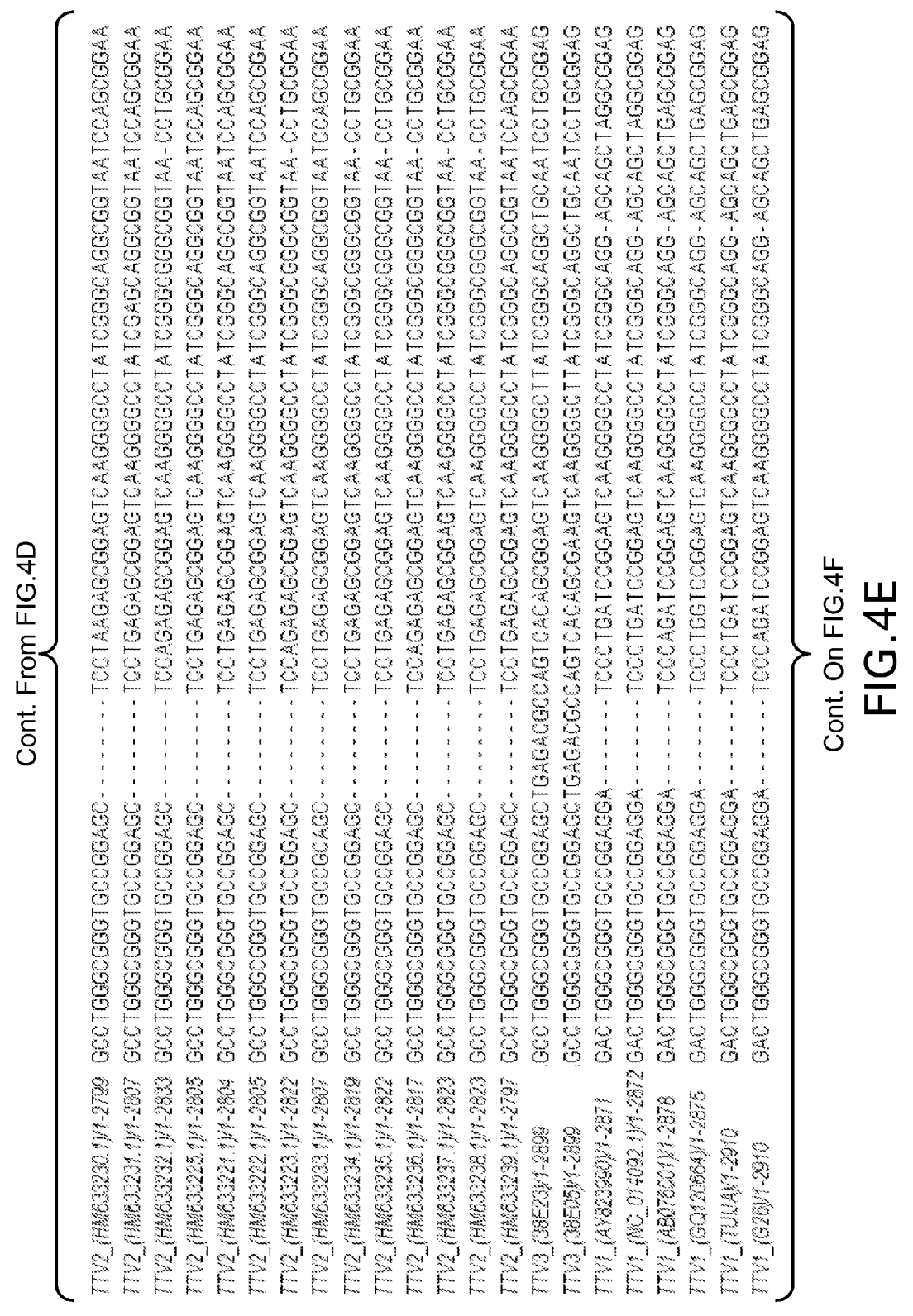
Figure 4F:
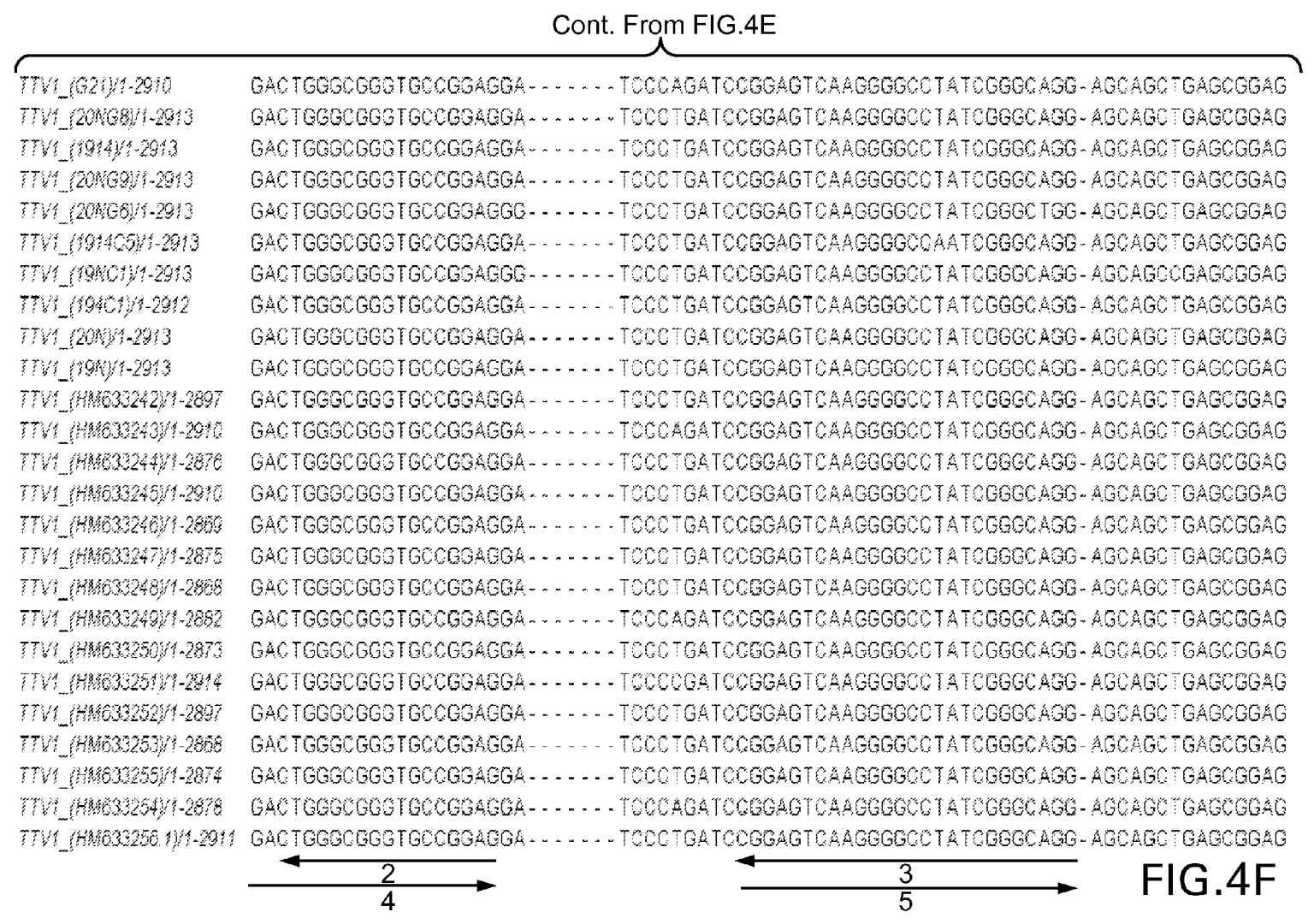

FIG. 4A-FIG. 4F provides a sequence alignment of 69 known sTTV-sequences and the arrows numbered 1-5 indicate where SEQ ID NO: 1, 2, 3, 4 and 5 are roughly located.

As can be seen from FIG. 4A-FIG. 4F, a primer set comprising a forward primer according to the invention binding to FDNA-TTV and a reverse primer according to the invention binding to RDNA-TTV-r1 or a primer set comprising a forward primer according to the invention binding to FDNA-TTV and a reverse primer according to the invention binding to RDNA-TTV-r2 are capable of giving a PCR-product in all cases, i.e. with all field isolates tested, regardless their geographical origin or their genotype.

As follows from FIG. 4A-FIG. 4F, a PCR-product generated by a primer set binding to FDNA-TTV and RDNA-TTV-r2 would have a length of roughly between 83 and 88 nucleotides. This depends of course on the exact length of the region between the two primers. And since the variability in the regions between the primers is high, even within the sTTV group, it is not possible to predict an exact length. However, the exact length of a PCR product is not important: only the absence or presence of a PCR-product is relevant, not its exact size.

An alternative to the time-consuming analysis of the potential PCR-product by means of conventional agarose or polyacrylamide gel electrophoresis is the use of the SYBR Green system (vide supra and infra). SYBR Green is a dye that intercalates with double-stranded (ds) DNA. This intercalation causes SYBR Green to fluoresce. Therefore, if the PCR reaction is done in the presence of SYBR Green, each new dsDNA copy would pick up an amount of SYBR Green and cause it to fluoresce. A real time PCR machine can detect this fluorescence and dedicated software can calculate Ct values from the intensity of the fluorescence. This allows for a direct quantification of the amount of cDNA made. (The use of SYBR Green however does not allow for the presence of an internal control that indicates if the reaction steps proceeded as expected). SYBR-Green based RT-PCR methods have been described by Mackay, I. M. et al.

The method above thus provides a way of selectively detecting the presence or absence of sTTV in a sample, regardless the geographic origin or the genotype of the TTV strain.

Thus, a first embodiment of the invention relates to a method for the detection of the presence of swine Torque Teno virus (sTTV) in a sample, characterised in that said method comprises the steps of a) performing a polymerase chain reaction (PCR) of said sample using a primer set comprising a forward primer that binds to a stretch of at least 14 consecutive nucleotides of an oligonucleotide FDNA-TTV having a sequence as depicted in SEQ ID NO.: 1, and a reverse primer that binds to a stretch of at least 14 consecutive nucleotides of an oligonucleotide RDNA-TTV-r1 having a sequence as depicted in SEQ ID NO.: 2 or a reverse primer that binds to a stretch of at least 14 consecutive nucleotides of an oligonucleotide RDNA-TTV-r2 having a sequence as depicted in SEQ ID NO.: 3 and b) examining the PCR amplification result of step (a)

In a preferred form of this embodiment, one primer of the primer set binds to the full length of the oligonucleotide FDNA-TTV having a sequence as depicted in SEQ ID NO.: 1 and the other primer of the primer set binds to the full length of the oligonucleotide RDNA-TTV-r1 having a sequence as depicted in SEQ ID NO.: 2 or to the full length of the oligonucleotide RDNA-TTV-r2 having a sequence as depicted in SEQ ID NO.: 3.

Merely as an example: a primer of the primer set that binds to the full length of the oligonucleotide FDNA-TTV having a sequence as depicted in SEQ ID NO.: 1 is e.g. a primer with a length of 22 nucleotides and having a sequence cgaatggctg agtttatgcc gc.

It will be noticed that e.g. in SEQ ID NO: 1, the nucleotide at position 2 is a S (i.e.: can be G or C). The S at position 2 is not of much influence when it comes to developing a suitable primer. It is located relatively far from the point where primer extension takes place. The primer will anneal both to DNA having a G and DNA having a C at that position. Therefore, a primer having a sequence cgaatggctg agtttatgcc gc and a primer having a sequence ccaatggctg agtttatgcc gc are both suitable. The skilled person would know how to correct the temperature of the PCR-steps to compensate for a possible mismatch.

Alternatively, a degenerate primer can be used, comprising both a primer having the sequence cgaatggctg agtttatgcc gc and a primer having the sequence ccaatggctg agtttatgcc gc.

Merely as another example: the nucleotide R at position 18 is of more relevance, since it is located close to the point where primer extension takes place. Therefore, it would be advisable to either use a shorter primer, such as cgaatggctg agtttat, or to use a degenerated primer comprising a primer having an A and a primer having a G at position 18.

For each of the sequences given in SEQ ID NO: 1, 2, 3, 4 and 5 there is a clear consensus sequence. This can immediately be seen from FIG. 4A-FIG. 4F.

beyond the selectivity of the PCR reaction described above. It relies on the use of a primer set comprising a forward primer that binds to a stretch of at least 14 consecutive nucleotides of an oligonucleotide FDNA-TTV having a sequence as depicted in SEQ ID NO.: 1 and a reverse primer that binds to a stretch of at least 14 consecutive nucleotides of an oligonucleotide RDNA-TTV-r2 having a sequence as depicted in SEQ ID NO.: 3, and a probe that binds to a stretch of at least 14 consecutive nucleotides of an oligonucleotide RDNA-TTV-r1 having a sequence as depicted in SEQ ID NO.: 2, according to the invention.

A probe that binds to a stretch of at least 14 consecutive nucleotides of an oligonucleotide RDNA-TTV-r1 differs from a primer that binds to a stretch of at least 14 consecutive nucleotides of an oligonucleotide RDNA-TTV-r1 in that such a probe is an oligonucleotide with a fluorophore and a quencher molecule attached to it. Several versions of such probes exist when it comes to the fluorophore or quencher used or the working mechanism behind the probe/quencher combination. Merely as an example, such probes are commercially available as TaqMan probes, Scorpions probes and Molecular Beacons probes (vide infra).

In this method using a probe, the detection can be done e.g. by using the probe according to the invention. This probe binds, as said above, in a selective manner with an internal sequence of the cDNA made in a PCR reaction using e.g. the FDNA-TTV/RDNA-TTV-r2 binding primer set according to the invention. For example in strain TTV2_(HM633239.1)/1-2797 (see FIG. 4A-FIG. 4F), the probe would e.g. anneal in a step b) to the cDNA RDNA-TTV-r2 region from position 380-396 of the alignment. This however happens only in case the amplified DNA is indeed of sTTV origin. In the unlikely case that the two selective primers would amplify non-TTV DNA, this would be noticed in step b, because the probe would not anneal to it. Therefore, the probe according to the invention makes the detection of sTTV even more specific than a mere PCR reaction. Moreover, the use of a probe avoids the use of gels for the detection of PCR products. And finally, the level of fluorescence detected in the real-time PCR thermal cycler is directly proportional to the fluorophore released and therefore the amount of DNA template present in the PCR (vide infra). This method is therefore very suitable in real-time PCR reactions.

```
The consensus sequence for SEQ ID NO: 1 is cgaatggctgagtttatgccgc

The consensus sequence for SEQ ID NO: 2 is ctgggcgggtgccggag

The consensus sequence for SEQ ID NO: 3 is cggagtcaaggggcctatcgggcagg

The consensus sequence for SEQ ID NO: 4 is tgtctagccgcctgggcgggtgccggag

The consensus sequence for SEQ ID NO: 5 is cggagtcaaggggcctatcgggcagg
```

The consensus sequences are the preferred sequences when designing primers binding to these sequences.

The following should be noted: in 38 of the sTTV sequences analysed and presented in FIG. 4A-FIG. 4F, the sequence of SEQ ID NO: 4 is ygtctarcmgmctgggcgggtgccgvag. However, in 31 of the sTTV sequences analysed and presented in FIG. 4A-FIG. 4F, the sequence of SEQ ID NO: 4 is ygtctarcgmctgggcgggtgccgvag due to a gap of one nucleotide. The gap is located relatively far from the point where primer extension takes place, so it should not necessarily be taken into account when designing a suitable primer.

A more efficient and selective method, for detecting the presence of the PCR product is a probe-based real-time PCR. This method basically relies on the PCR methods described above, but it has a level of selectivity that goes TaqMan based real-time RT-PCR methods are a development by Applied Biosystems, 850 Lincoln Centre Drive, Foster City, Calif. 94404, USA.

TaqMan based real-time RT-PCR methods are described i.a. in literature references 8, 10 and 33. Real-time RT-PCR methods based upon Scorpions and Molecular beacons are available through PREMIER Biosoft International, 3786 Corina Way, Palo Alto Calif. 94303-4504, USA.

The use of real-time PCR on the basis of Molecular Beacons is described in detail in i.a: Molecular Beacons; A New Tool to Identify Point Mutations and to Analyze Gene Expression in *Mycobacterium tuberculosis* by Manganelli, R., Tyagi, S, and Smith, I., in: Methods in Molecular Medicine, vol. 54: page 295-310, *Mycobacterium Tuberculosis* Protocols, Edited by: T. Parish and N. G. Stoker© Humana Press Inc., Totowa, N.J.

TaqMan probes consist of a fluorophore covalently attached to the 5'-end of the oligonucleotide probe and a quencher at the 3'-end. Several different fluorophores (e.g. 6-carboxyfluorescein, acronym: FAM, or tetrachlorofluorescin, acronym: TET) and quenchers (e.g. tetramethylrhodamine, acronym: TAMRA, or dihydrocyclopyrroloindole tripeptide minor groove binder, acronym: MGB) are available. The quencher molecule quenches the fluorescence emitted by the fluorophore when excited by the cycler's light source via FRET (Fluorescence Resonance Energy Transfer). As long as the fluorophore and the quencher are in proximity, quenching inhibits any fluorescence signals.

TaqMan probes are designed such that they anneal within a DNA region amplified by a specific set of primers. As Taq polymerase extends the primer and synthesizes the nascent strand, the 5' to 3' exonuclease activity of the polymerase degrades the probe that has annealed to the template. Degradation of the probe releases the fluorophore from it and breaks the close proximity to the quencher, thus relieving the quenching effect and allowing fluorescence of the fluorophore. Hence, fluorescence detected in the real-time PCR thermal cycler is directly proportional to the fluorophore released and the amount of DNA template present in the PCR.

Taqman probes are preferred probes for use in the methods and diagnostic tools according to the invention.

In fact, the Taqman probe Probe TTV-r1 described here is an oligonucleotide binding to a DNA sequence as depicted in SEQ ID NO.: 2, however with a fluorophore and a quencher attached to it. But as explained (vide supra), the probe can also be a shorter or longer oligonucleotide binding to a stretch of at least 14 consecutive nucleotides of an oligonucleotide RDNA-TTV-r1 having a sequence as depicted in SEQ ID NO.: 2.

Since in this method both the annealing of the primers and the probe takes place in one process, the development of a color reaction takes place at practically the same moment as the DNA amplification. Therefore, such reaction is referred to as a real-time PCR reaction.

Thus, another preferred form of this embodiment relates to a method for the detection of the presence of swine Torque Teno virus (sTTV) in a sample, characterised in that said method comprises the steps of
a) performing a polymerase chain reaction (PCR) of said sample using a primer set comprising a forward primer that binds to a stretch of at least 14 consecutive nucleotides of an oligonucleotide FDNA-TTV having a sequence as depicted in SEQ ID NO.: 1 and a reverse primer that binds to a stretch of at least 14 consecutive nucleotides of an oligonucleotide RDNA-TTV-r2 having a sequence as depicted in SEQ ID NO.: 3 and
b) examining the PCR amplification result of step (a) using a probe binding to a stretch of at least 14 consecutive nucleotides of an oligonucleotide RDNA-TTV-r1 having a sequence as depicted in SEQ ID NO.: 2.

In a more preferred form of this embodiment, one primer of the primer set binds to the full length of the oligonucleotide FDNA-TTV having a sequence as depicted in SEQ ID NO.: 1 and the other primer of the primer set binds to the full length of the oligonucleotide RDNA-TTV-r2 having a sequence as depicted in SEQ ID NO.: 3.

In another more preferred form of this embodiment, the probe binds to the full length of the oligonucleotide RDNA-TTV-r1 having a sequence as depicted in SEQ ID NO.: 2.

As mentioned above, sTTV could be present in tissue with or without replicating there. It is known that TTV is found in practically all tissues and organs, but it is unknown if it is merely found in a tissue because it was transported to that tissue by the blood or if it is actively replicating there.

Therefore, a test that could discriminate between the mere presence of sTTV in e.g. a tissue and active replication of the virus in that tissue is highly needed.

Such a test would additionally make it possible to detect if traces of sTTV in cell culture are or aren't in an inactivated form: certainty about the lack of sTTV viral replication would make viral vaccine production in cell culture safer.

The genome replication of TTV proceeds through a rolling circle model: during replication a positive-stranded ssDNA is made using the negative strand genomic viral DNA strand as a template, and this positive stranded DNA in turn serves as a template to make new negative-strand DNA. In principle, the positive-stranded DNA could be used for the detection of replication; a strand-specific PCR-test (ssPCR) using primers that bind specifically to the positive DNA strand could then be used to show DNA replication. A problem however arises when TTV enters a non-permissive cell, i.e. a cell that does not support the full, productive, replicative cycle of the virus including the formation of new virus particles. In such non-permissive cells, the cellular mechanism would nevertheless start replicating viral ssDNA and consequently positive-strand DNA will be formed, incorrectly suggesting productive viral replication. Therefore, an ssPCR is not a reliable test to confirm productive viral replication.

A more reliable indicator for viral replication is the presence of sTTV mRNA since active virus replication reveals itself through the appearance of mRNA's. Such mRNA's could then be detected by means of a reverse transcriptase polymerase chain reaction, further referred to as RT-PCR.

However, the extremely variability in genome sequence for the various sTTV's make it very difficult to identify universal primers for use in a reverse transcriptase polymerase chain reaction (RT-PCR).

A second problem is posed by the fact that not much is known about the RNA splicing patterns in sTTV's, except for the fact that there appears to be a significant variance in the splicing pattern between various sTTV's. Due to the splicing characteristics of sTTV viral replication, it may well be that some primers can not be used at all, since they anneal to regions that are lost upon RNA splicing. After splicing of the mRNA, such regions would be lost and consequently no RT-PCR product would be found. And this in turn would lead to a false indication that no viral sTTV replication takes place.

Surprisingly it was found now that the regions RDNA-TTV-r1 and RDNA-TTV-r2 to which the PCR-primers bind, are also present in the mRNA of sTTV's. Even more surprisingly, these regions were found to be located outside regions that are spliced out during the mRNA splicing process. Therefore, these regions are always present in mRNA of sTTV's, regardless the mRNA splicing pattern followed by any sTTV.

This means that regions RDNA-TTV-r1 and to RDNA-TTV-r2 can also be used to develop forward primers in an RT-PCR reaction for the detection of mRNA during viral replication of sTTV's regardless their geographical origin or their genotype.

This test thus allows for the first time to discriminate between the mere presence of sTTV ssDNA in a tissue, and active replication of the virus in that tissue.

A reverse transcriptase polymerase chain reaction (RT-PCR) comprises two reaction steps. In a first step, one of the primers of the primer set is allowed to bind to TTV-RNA, and this complex forms the starting point for the synthesis of a cDNA strand of the RNA strand by the enzyme reverse transcriptase (an RNA-dependent DNA polymerase) in the presence of the four DNA building blocks A, T, G and C.

In a second step, the thus-formed RNA-DNA hybrid is heated in order to denature the hybrid, followed by cooling in order to allow the other primer of the primer set to bind to the cDNA strand. This other primer then functions as the starting point for the synthesis of the second DNA strand by a DNA polymerase, again in the presence of the DNA building blocks.

Depending on the amount of sTTV-RNA in the sample (provided that it is present), several PCR-cycles will have to be made before there is sufficient material to be detected. An average of between 30 and 45 cycles would not be unusual. The skilled artisan would be able, on the basis of the sequences of the primers and the probe, to determine the optimal temperature conditions for the various steps of the PCR-cycle using e.g. the formulae given above and in text books mentioned above. (vide supra).

As mentioned above, suitable forward primers are the primers that are complementary to RDNA-TTV-r1 and RDNA-TTV-r2.

Such forward primers according to the invention bind to a stretch of at least 14 consecutive nucleotides of an oligonucleotide FRNA-a having a sequence as depicted in SEQ ID NO.: 4 or a stretch of at least 14 consecutive nucleotides of an oligonucleotide FRNA-b having a sequence as depicted in SEQ ID NO.: 5.

As a reverse primer, a primer is used that binds to the poly-A tail of mRNAs. Such a primer would thus comprise a poly-T stretch. Such a primer preferably consists of at least 14 consecutive T's.

In order to avoid random binding of such primers to any part of the poly-A tail, the reverse primer preferably carries a nucleotide G, a nucleotide C or a nucleotide A at the 3'-end of the poly-T stretch. This would allow for specific binding of the primer to the 5'-end of the poly-A tail. If the characteristic of the last nucleotide before the poly-A-tail is known from sequencing of the virus, the nucleotide at the 3'-end of the poly-T stretch can be made complementary to that last nucleotide. If the characteristic is not known, a mixture of three poly-T primers, each having either a G, a C or an A at the 3'-end of the poly-T stretch can successfully be used.

Thus, a reverse primer according to the invention comprises at least a stretch of at least 14 consecutive nucleotides binding to the most 5'-terminal nucleotides of an oligonucleotide RRNA-1 having a sequence as depicted in SEQ ID NO.: 6, an oligonucleotide RRNA-2 having a sequence as depicted in SEQ ID NO.: 7 or an oligonucleotide RRNA-3 having a sequence as depicted in SEQ ID NO.: 8.

Merely as an example; a reverse primer according to the invention and binding to a stretch of at least 14 consecutive 5'-terminal nucleotides of an oligonucleotide RRNA-1 having a sequence as depicted in SEQ ID NO.: 6 could e.g. have a nucleotide sequence TTTTTTTTTTTTTTA, TTTTTTTTTTTTTTTTTTA or TTTTTTTTTTTTTTTTTTTTTTTTA The melting temperature of T/A duplexes is relatively low. Thus, if desired, primers binding to the poly-A tail can be extended at the 5'-end with a known but random sequence of e.g. 15 nucleotides. If such a 5'-extended primer is used, a successful annealing between the poly-T part of the primer and the poly-A tail of the mRNA needs to be successful in only one PCR-cycle. In subsequent cycles, the annealing reaction would be much more efficient due to the fact that now a second primer can be used that is complementary to the 5'-extension of the poly-T primer.

Thus, another embodiment of the present invention relates to a method for the detection of the presence of replicating sTTV in a sample, characterised in that said method comprises the steps of
a) performing a reverse transcriptase polymerase chain reaction (RT-PCR) of said sample using a primer set comprising a forward primer that binds to a stretch of at least 14 consecutive nucleotides of an oligonucleotide FRNA-a having a sequence as depicted in SEQ ID NO.: 4 or a forward primer that binds to a stretch of at least 14 consecutive nucleotides of an oligonucleotide FRNA-b having a sequence as depicted in SEQ ID NO.: 5, and at least one reverse primer that binds to a stretch of at least 14 consecutive 5'-terminal nucleotides of an oligonucleotide RRNA-1 having a sequence as depicted in SEQ ID NO.: 6, an oligonucleotide RRNA-2 having a sequence as depicted in SEQ ID NO.: 7 or an oligonucleotide RRNA-3 having a sequence as depicted in SEQ ID NO.: 8, and
b) examining the RT-PCR amplification result of step (a)

As a forward primer, preferably a primer binding to a stretch of at least 14 consecutive nucleotides of an oligonucleotide FRNA-a is used: this would allow the use of a probe binding to a stretch of at least 14 consecutive nucleotides of an oligonucleotide FRNA-b for the detection of a RT-PCR product in a real-time RT-PCR reaction.

Thus, a preferred form of this embodiment relates to a method for the detection of the presence of replicating sTTV according to the invention, characterised in that said forward primer binds to a stretch of at least 14 consecutive nucleotides of an oligonucleotide FRNA-a having a sequence as depicted in SEQ ID NO.: 4

The probe, basically binding to a stretch of at least 14 consecutive nucleotides of an oligonucleotide FRNA-b having a sequence as depicted in SEQ ID NO.: 5 comprises a quencher molecule and a fluorophore.

Thus, a more preferred form of this embodiment relates to a method for the detection of the presence of replicating sTTV according to the invention, characterised in that said method additionally comprises the step of examining the PCR amplification result of step (a) using a probe binding to a stretch of at least 14 consecutive nucleotides of an oligonucleotide FRNA-b having a sequence as depicted in SEQ ID NO.: 5.

Ideally, the method indicated above for the detection of sTTV DNA and the method indicated above for the detection of sTTV viral replication would be applied simultaneously in one vial. This would allow for the simultaneous detection of both the presence of sTTV DNA and sTTV viral replication.

However, care should be taken that the primers for the detection of DNA and RNA are correctly selected. If primers binding to FDNA-TTV and RDNA-TTV-r2 are used for the detection of DNA, the use of a primer binding to FRNA-b for the detection of mRNA should be avoided, because in that case, the primer binding to FRNA-b would anneal to the primer binding to RDNA-TTV-r2. For the same reason, if primers binding to FDNA-TTV and RDNA-TTV-r1 are used for the detection of DNA, the use of a primer binding to FRNA-a for the detection of mRNA should be avoided, because in that case, the primer binding to FRNA-a would anneal to the primer binding to RDNA-TTV-r1.

For the same reason, if the primer binding to RDNA-TTV-r2 is used for the detection of DNA, and primer binding to FRNA-a is used for the detection of RNA, then probes complementary to RDNA-TTV-r1 and FRNA-b can not be used for the detection of DNA and RNA. Therefore, the simultaneous detection of the respective PCR-products and RT-PCR products can not be done by using the probes according to the invention. Thus these products should be analysed by other means such as gel electrophoresis.

Thus, another embodiment of the present invention relates to a method for the detection of the presence of replicating sTTV in a sample, characterised in that said method comprises the simultaneous steps of
a) performing a polymerase chain reaction (PCR) of said sample using a primer set comprising a forward primer that binds to a stretch of at least 14 consecutive nucleotides of an oligonucleotide FDNA-TTV having a sequence as depicted in SEQ ID NO.: 1 and a reverse primer that binds to a stretch of at least 14 consecutive nucleotides of an oligonucleotide RDNA-TTV-r2 having a sequence as depicted in SEQ ID NO.: 3 and
b) performing a reverse transcriptase polymerase chain reaction (RT-PCR) of said sample using a primer set comprising a forward primer that binds to a stretch of at least 14 consecutive nucleotides of an oligonucleotide FRNA-a having a sequence as depicted in SEQ ID NO.: 4 and at least one reverse primer that binds to a stretch of at least 14 consecutive nucleotides of an oligonucleotide RRNA-1, 2 or 3, having a sequence as depicted in SEQ ID NO.: 6, in SEQ ID NO.: 7 or in SEQ ID NO.: 8 and
c) examining the PCR amplification result of steps a) and b)

And again another embodiment of the present invention relates to a method for the detection of the presence of replicating sTTV in a sample, characterised in that said method comprises the simultaneous steps of
a) performing a polymerase chain reaction (PCR) of said sample using a primer set comprising a forward primer that binds to a stretch of at least 14 consecutive nucleotides of an oligonucleotide FDNA-TTV having a sequence as depicted in SEQ ID NO.: 1 and a reverse primer that binds to a stretch of at least 14 consecutive nucleotides of an oligonucleotide RDNA-TTV-r1 having a sequence as depicted in SEQ ID NO.: 2 and
b) performing a reverse transcriptase polymerase chain reaction (RT-PCR) of said sample using a primer set comprising a forward primer that binds to a stretch of at least 14 consecutive nucleotides of an oligonucleotide FRNA-b having a sequence as depicted in SEQ ID NO.: 5 and at least one reverse primer that binds to a stretch of at least 14 consecutive nucleotides of an oligonucleotide RRNA having a sequence as depicted in SEQ ID NO.: 6, in SEQ ID NO.: 7 or in SEQ ID NO.: 8 and
c) examining the (RT)-PCR amplification result of steps a) and b)

As discussed for the DNA PCR-product generated by the primer set binding to respectively FDNA-TTV and RDNA-TTV-r2 above, an exact length of the RT-PCR products when using e.g. a primer set comprising a forward primer binding to FRNA-a and a reverse primer binding to RRNA-1 can not be given. First of all; since the variability in the regions between the primers is high, even within the sTTV group, it is not possible to predict an exact length for these products. And moreover, for RT-PCR products, this is even more unpredictable since so many splice variants are known for TTV's. However, again, the exact length of an RT-PCR product is not important: only the absence or presence of a RT-PCR-product is relevant, not its exact size.

Methods according to the invention that rely on RT-PCR can be further improved by adding a so-called internal control RNA (IC RNA). In fact, the internal control is a parallel experiment, in which an amount of a control RNA is added to the test sample, as well as primers and a probe that are specific for that control RNA (IC-RNA). (Or alternatively, though less preferred, the control RNA and the primers and probe are tested separately in a parallel RT-PCR test). Such primers and probe should be non-TTV related; if they would be TTV-related they might interfere with the TTV-specific part of the method.

It is clear that the colour of the fluorophore of the TTV-probe and the fluorophore of the non-TTV probe must be different, in order to discriminated between TTV-specific fluorescence and IC-RNA-specific fluorescence.

Since all the components for a successful reaction showing the presence of the IC-RNA are present, there will be a specific fluorescence, indicating that the various process steps were successful. Preferably, the IC-RNA test is performed in the same test tube as the sTTV-detection test. Thus, if fluorescence of the IC-RNA specific fluorophore is detected, the test as such is reliable, and if in addition fluorescence of the TTV specific fluorophore is detected, that proves the presence of TTV-material.

If fluorescence of the IC-RNA specific fluorophore is detected, but no fluorescence of the TTV specific fluorophore is detected, that proves the absence of TTV-material.

If no fluorescence of the IC-RNA specific fluorophore is detected, the test is not reliable and should not be taken into account.

Thus, the use of an internal control is important to exclude false negative results due to e.g. inefficient RNA isolation, inefficient reverse transcriptase reaction or inhibition of PCR.

In principle, a synthetic RNA can be used as the starting material for the internal control. As an alternative to synthetic fragments of RNA, housekeeping genes or different genes of the host or from different pathogens can be used as internal control. Their unknown and changing concentration, instability and bio safety concerns make them however more difficult to handle and integrate in the PCR assay than in vitro transcribed RNA.

For this reasons, a preferred internal control system is the universal heterologous internal control system designed by Hoffmann et al. It is based on RNA and could easily be adapted and integrated in the assay to check for successful RNA extraction and RT-PCR.

Thus, an even more preferred form of this embodiment relates to a method according to the invention, characterised in that the step of performing the real-time RT-PCR reaction of said method additionally uses at least one additional non-TTV related primer set and at least one additional non-TTV related RNA template.

If quantification of the PCR reaction is required, separate parallel tests can be run in which known amounts of TTV-DNA or TTV-mRNA and the primers and probe according to the present invention are present. This would allow for standard curves to be drawn that provide a relation between the amount of DNA or RNA in the parallel test and the number of cycles required to reach the fluorescence detection threshold. These standard curves can then subsequently be used to determine the unknown amount of TTV-DNA or TTV-mRNA in the sample.

Therefore, a method according to the invention to which separate parallel tests are run in order to make standard curves that are subsequently used for the quantification of the amount of TTV-DNA or TTV-mRNA in a sample, is referred to as a quantitative method.

It is clear that the biological material is preferably submitted to further purification steps.

Since the method for the detection of sTTV is based upon viral ssDNA and/or mRNA, this ssDNA and RNA is preferably purified from the sample to a certain extent. Purification in this respect means that material in the sample other than TTV-DNA or mRNA is to a certain extent removed from the sample before the sample is submitted to a method according to the invention. Such purification can e.g. comprise de-proteinisation, removal of cell debris, DNA-extraction, RNA-extraction and the like.

Thus, a still even more preferred form of the present invention relates to a method according to the invention, characterised in that said method comprises an RNA and/or DNA purification step preceding step a).

Another embodiment of the present invention relates to a primer set comprising a forward primer that binds to a stretch of at least 14 consecutive nucleotides of an oligonucleotide FDNA-TTV having a sequence as depicted in SEQ ID NO.: 1 and a reverse primer that binds to a stretch of at least 14 consecutive nucleotides of an oligonucleotide RDNA-TTV-r1 having a sequence as depicted in SEQ ID NO.: 2 or a reverse primer that binds to a stretch of at least 14 consecutive nucleotides of an oligonucleotide RDNA-TTV-r2 having a sequence as depicted in SEQ ID NO.: 3

A further embodiment of the present invention relates to a primer set comprising a forward primer that binds to a stretch of at least 14 consecutive nucleotides of an oligonucleotide FRNA-a having a sequence as depicted in SEQ ID NO.: 4 or a forward primer that binds to a stretch of at least 14 consecutive nucleotides of an oligonucleotide FRNA-b having a sequence as depicted in SEQ ID NO.: 5, and at least one reverse primer that binds to a stretch of at least 14 consecutive 5'-terminal nucleotides of an oligonucleotide RRNA-1 having a sequence as depicted in SEQ ID NO.: 6, an oligonucleotide RRNA-2 having a sequence as depicted in SEQ ID NO.: 7 or an oligonucleotide RRNA-3 having a sequence as depicted in SEQ ID NO.: 8

Still another embodiment of the present invention relates to a probe binding to a stretch of at least 14 consecutive nucleotides of an oligonucleotide RDNA-TTV-r1 having a sequence as depicted in SEQ ID NO.: 2, or to a stretch of at least 14 consecutive nucleotides of an oligonucleotide FRNA-b having a sequence as depicted in SEQ ID NO.: 5.

Again another embodiment of the present invention relates to diagnostic test kits for the detection of the presence of swine Torque Teno virus (sTTV) in a sample. Such kits allow for the methods according to the invention to be practised.

Thus, a first form of this embodiment relates to a diagnostic test kit for the detection of the presence of swine Torque Teno virus (sTTV) in a sample, characterised in that said kit comprises at least a primer set comprising a forward primer that binds to a stretch of at least 14 consecutive nucleotides of an oligonucleotide FDNA-TTV having a sequence as depicted in SEQ ID NO.: 1 and a reverse primer that binds to a stretch of at least 14 consecutive nucleotides of an oligonucleotide RDNA-TTV-r1 having a sequence as depicted in SEQ ID NO.: 2 or a reverse primer that binds to a stretch of at least 14 consecutive nucleotides of an oligonucleotide RDNA-TTV-r2 having a sequence as depicted in SEQ ID NO.: 3

In a preferred form of this embodiment, said diagnostic test kit for the detection of the presence of sTTV additionally comprises a probe binding to a stretch of at least 14 consecutive nucleotides of an oligonucleotide RDNA-TTV-r1 having a sequence as depicted in SEQ ID NO.: 2.

Again another embodiment relates to a diagnostic test kit for the detection of the presence of replicating sTTV in a sample, characterised in that said kit comprises a primer set comprising a forward primer that binds to a stretch of at least 14 consecutive nucleotides of an oligonucleotide FRNA-a having a sequence as depicted in SEQ ID NO.: 4 or a forward primer that binds to a stretch of at least 14 consecutive nucleotides of an oligonucleotide FRNA-b having a sequence as depicted in SEQ ID NO.: 5, and at least one reverse primer that binds to a stretch of at least 14 consecutive 5'-terminal nucleotides of an oligonucleotide RRNA-1 having a sequence as depicted in SEQ ID NO.: 6, an oligonucleotide RRNA-2 having a sequence as depicted in SEQ ID NO.: 7 or an oligonucleotide RRNA-3 having a sequence as depicted in SEQ ID NO.: 8.

In a preferred form of this embodiment, said diagnostic test kit for the detection of the presence of replicating sTTV additionally comprises a probe binding to a stretch of at least 14 consecutive nucleotides of an oligonucleotide FRNA-b having a sequence as depicted in SEQ ID NO.: 5.

These various primers and probes may be present in the kit in separate vials. They may also be present in one and the same vial. They could, for ease of manipulation and in order to avoid unnecessary risk of contamination, even be present in the test vial to which the sample is added.

They would preferably be present in a dried form, in order to keep them stable under room storage conditions.

Still another embodiment relates to a diagnostic test kit for the simultaneous detection of the presence of sTTV ssDNA and sTTV virus replication in a sample, characterised in that said kit comprises a primer set comprising a forward primer that binds to a stretch of at least 14 consecutive nucleotides of an oligonucleotide FDNA-TTV having a sequence as depicted in SEQ ID NO.: 1 and a reverse primer that binds to a stretch of at least 14 consecutive nucleotides of an oligonucleotide RDNA-TTV-r2 having a sequence as depicted in SEQ ID NO.: 3 and a primer set comprising a forward primer that binds to a stretch of at least 14 consecutive nucleotides of an oligonucleotide FRNA-a having a sequence as depicted in SEQ ID NO.: 4 and at least one reverse primer that binds to a stretch of at least 14 consecutive nucleotides of an oligonucleotide RRNA having a sequence as depicted in SEQ ID NO.: 6, in SEQ ID NO.: 7 or in SEQ ID NO.: 8.

Again another embodiment relates to a diagnostic test kit for the simultaneous detection of the presence of sTTV ssDNA and sTTV virus replication in a sample, characterised in that said kit comprises a primer set comprising a forward primer that binds to a stretch of at least 14 consecutive nucleotides of an oligonucleotide FDNA-TTV having a sequence as depicted in SEQ ID NO.: 1 and a reverse primer that binds to a stretch of at least 14 consecutive nucleotides of an oligonucleotide RDNA-TTV-r1 having a sequence as depicted in SEQ ID NO.: 2 and a primer set comprising a forward primer that binds to a stretch of at least 14 consecutive nucleotides of an oligonucleotide FRNA-b having a sequence as depicted in SEQ ID NO.: 5 and at least one reverse primer that binds to a stretch of at least 14 consecutive nucleotides of an oligonucleotide RRNA having a sequence as depicted in SEQ ID NO.: 6, in SEQ ID NO.: 7 or in SEQ ID NO.: 8.

A diagnostic test kit according to the invention may additionally comprise a reverse transcriptase and/or a thermo stable DNA polymerase. These enzymes are necessary to perform a real-time RT-PCR and for ease of use they might thus already be incorporated in the diagnostic test kit.

If an internal control of the real-time RT-PCR is required, a second set of primers and probe, in this case non-TTV primers and a non-TTV RNA template and a non-TTV probe as discussed above, as well as the IC-RNA may be included in the diagnostic test kit. It goes without saying that the four DNA building blocks and the necessary buffers may additionally be included in the diagnostic test kit as well.

If quantification of the (RT)-PCR reaction is required, parallel tests can be run in which known amounts of TTV-RNA and/or TTV-DNA and the primers and probes according to the present invention are present. This would allow for standard curves to be drawn that provide a relation between the amount of RNA and/or DNA in the parallel test and the number of cycles required to reach the fluorescence threshold. These standard curves can then be used to determine the amount of TTV-RNA and/or TTV-DNA in the sample. Therefore, preferably the diagnostic test kit additionally comprises known amounts of TTV-RNA and/or TTV-DNA that allow for quantification to be made.

Hereunder, examples of how to perform the method according to the invention are given. It goes without saying that the examples should not be considered to limit the scope of the invention in any way.

Legend To The Figures.

Figure 1B:
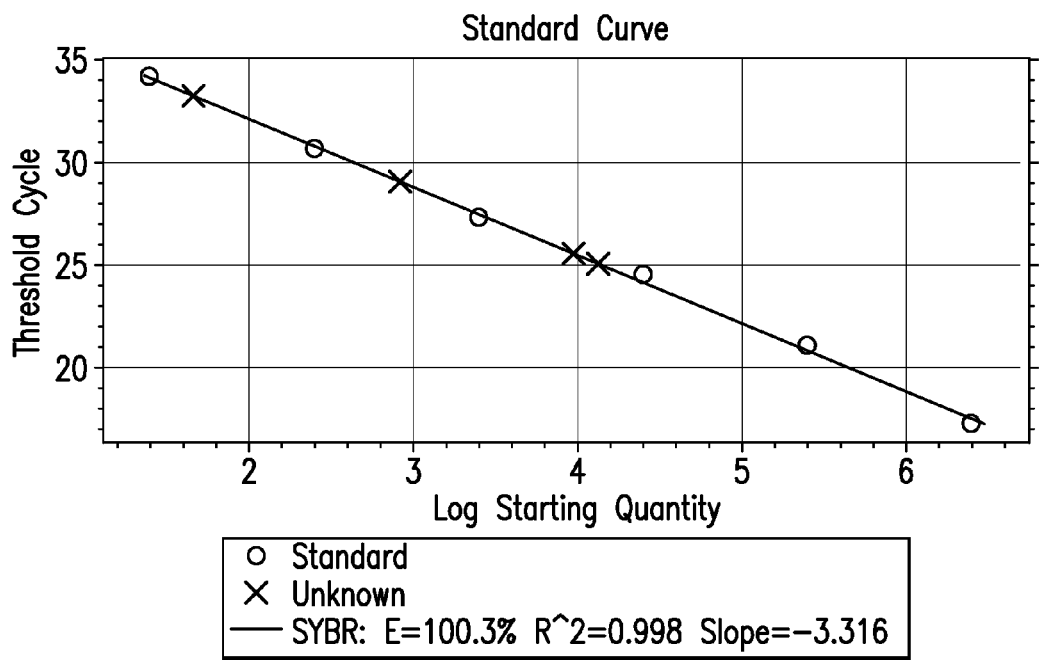

FIG. 1: amplification curve (FIG. 1a) and standard curve (FIG. 1b) chart of a broad spectrum qPCR for porcine TTV. In the amplification chart the grey curves represent the standard dilution series and the black curves represent the samples. In the standard curve chart the dots represent the standard dilution series and the crosses represent the samples.

Figure 2:
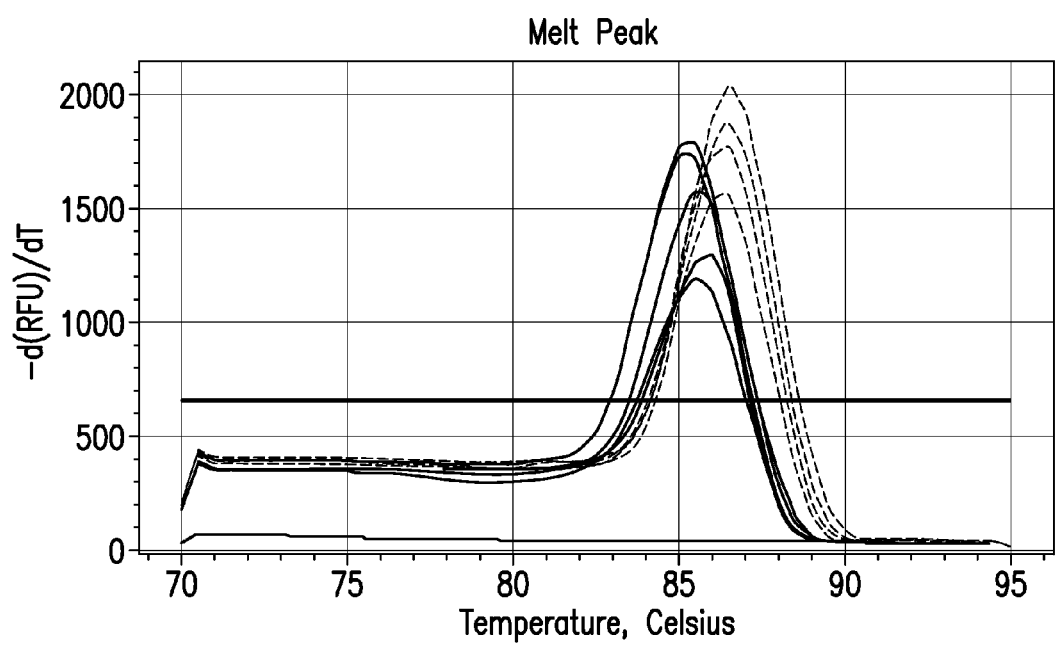

FIG. 2: melt peaks of the amplicons. The grey curves represent the standard dilution series and the black curves represent the samples. All samples showed one peak with a melting temperature between 85.0° C. and 86.5° C., indicating that the measured fluorescence was derived from only the PCR product.

FIG. 3: schematic drawing of plasmid TTV008 comprising 323 basepairs of an sTTV genotype 2 (sTTV2) virus.

FIG. 4A-FIG. 4F: sequence alignment of 69 known sTTV-sequences. The arrows numbered 1-5 indicate where SEQ ID NO: 1, 2, 3, 4 and 5 are roughly located.

Literature.

Biagini, P., Gallian, P., Attoui, H., Touinssi, M., Cantaloube, J.-F., de Micco, P. & de Lamballerie, X. (2001). Genetic analysis of full-length genomes and subgenomic sequences of TT virus-like mini virus human isolates. *J Gen Virol* 82, 379-383.

Cortey, M., Macera, L., Segales, J. & Kekarainen, T. (2010). Genetic variability and phylogeny of Torque teno sus virus 1 (TTSuV1) and 2 (TTSuV2) based on complete genomes. *Vet Microbiol* 148, 125-31.

Dieffenbach & Dreksler; PCR primers, a laboratory manual. ISBN 0-87969-447-5 (1995)

Ellis, J. A., Allan, G. & Krakowka, S. (2008). Effect of coinfection with genogroup 1 porcine torque teno virus on porcine circovirus type 2-associated postweaning multisystemic wasting syndrome in gnotobiotic pigs. *Am J Vet Res* 69, 1608-14.

Hijikata, M., Iwata, K., Ohta, Y., Nakao, K., Matsumoto, oto, M., Matsumoto, H., Kanai, K., Baba, K., Samokhvalov, E. I. & Mishiro, S. (1999). Genotypes of TT virus (TTV) compared between liver disease patients and healthy individuals using a new PCR system capable of differentiating 1a and 1b types from others*. *Arch Virol* 144, 2345-54.

Hoffmann, B., K. Depner, H. Schirrmeier, and M. Beer. 2006. A universal heterologous internal control system for duplex real-time RT-PCR assays used in a detection system for pestiviruses. J. Virol. Methods. 136:200-209.

Huang, Y. W., Ni, Y. Y., Dryman, B. A. & Meng, X. J. (2010). Multiple infection of porcine Torque teno virus in a single pig and characterization of the full-length genomic sequences of four U.S. prototype PTTV strains: implication for genotyping of PTTV. *Virology* 396, 289-97.

Kakkola, L., Tommiska, J., Boele, L. C. L., Miettinen, S., Blom, T., Kekarainen, T., Qiu, J., Pintel, D., Hoeben, R. C., Hedman, K. & Soderlund-Venermo, M. (2007). Construction and biological activity of a full-length molecular clone of human Torque teno virus (TTV) genotype 6. *FEBS Journal* 274, 4719-4730.

Kamahora, T., Hino, S. & Miyata, H. (2000). Three Spliced mRNAs of TT Virus Transcribed from a Plasmid Containing the Entire Genome in COS1 Cells. *J Virol* 74, 9980-9986.

Kekarainen, T., Sibila, M., Segale & és, J. (2006). Prevalence of swine Torque teno virus in post weaning multisystemic wasting syndrome (PMWS)-affected and non-PMWS-affected pigs in Spain. *J Gen Virol* 87, 833-837.

Leary, T. P., Erker, J. C., Chalmers, M. L., Desai, S. M. & Mushahwar, I. K. (1999). Improved detection systems for TT virus reveal high prevalence in humans, non-human primates and farm animals. *J. Gen Virol* 80, 2115-2120.

Leppik, L., Gunst, K., Lehtinen, M., Dillner, J., Streker, K. & de Villiers, E. M. (2007). In vivo and in vitro intragenomic rearrangement of TT viruses. *J Virol* 81, 9346-56.

Mankertz, A. & Hillenbrand, B. (2001). Replication of porcine circovirus type 1 requires two proteins encoded by the viral rep gene. *Virology* 279, 429-38.

Mackay, I. M., K. E. Arden, A. Nitsche. 2002 "Real-time PCR in virology". Nucleic Acids Res. 30 (6): 1292-305.

Mankertz, A., Caliskan, R., Hattermann, K., Hillenbrand, B., Kurzendoerfer, P., Mueller, B., Schmitt, C., Steinfeldt, T. & Finsterbusch, T. (2004). Molecular biology of Porcine circovirus: analyses of gene expression and viral replication. *Vet Microbiol* 98, 81-8.

Martinez, L., Kekarainen, T., Sibila, M., Ruiz-Fons, F., Vidal, D., Gortazar, C. & Segalés, J. (2006). Torque teno virus (TTV) is highly prevalent in the European wild boar (*Sus scrofa*). *Vet Microbiol* 118, 223-229.

Mueller, B., Maerz, A., Doberstein, K., Finsterbusch, T. & Mankertz, A. (2008). Gene expression of the human Torque Teno Virus isolate P/1C1. *Virology*.

Niel, C., Diniz-Mendes, L. & Devalle, S. (2005). Rolling-circle amplification of Torque teno virus (TTV) complete genomes from human and swine sera and identification of a novel swine TTV genogroup. *J Gen Virol* 86, 1343-7.

Nishizawa T, Okamoto H, Konishi K, Yoshizawa H, Miyakawa Y, Mayumi M. (1997). Biochem Biophys Res Commun 241: 92-97

Okamoto, H., Nishizawa, T., Tawara, A., Takahashi, M., Kishimoto, J., Sai, T. & Sugai, Y. (2000). TT Virus mRNAs Detected in the Bone Marrow Cells from an Infected Individual. *Biochem Biophys Res Commun* 279, 700-707.

Okamoto, H., Takahashi, M., Nishizawa, T., Tawara, A., Fukai, K., Muramatsu, U., Naito, Y. & Yoshikawa, A. (2002). Genomic characterization of TT viruses (TTVs) in pigs, cats and dogs and their relatedness with species-specific TTVs in primates and tupaias. *J Gen Virol* 83, 1291-7.

Okamoto, H. (2009). History of discoveries and pathogenicity of TT viruses. *Curr Top Microbiol Immunol* 331, 1-20.

Qiu, J., Kakkola, L., Cheng, F., Ye, C., Soderlund-Venermo, M., Hedman, K. & Pintel, D. J. (2005). Human Circovirus TT Virus Genotype 6 Expresses Six Proteins following Transfection of a Full-Length Clone. *J Virol* 79, 6505-6510.

Real-Time PCR: Current Technology and Applications, Publisher: Caister Academic Press, Editor: Julie Logan, Kirstin Edwards and Nick Saunders Applied and Functional Genomics, Health Protection Agency, London, ISBN: 978-1-904455-39-4

Sambrook, J. et al. Molecular cloning: a laboratory manual, 2nd edition, Cold Spring Harbor. ISBN 0-87969-309-6, Taira, O., Ogawa, H., Nagao, A., Tuchiya, K., Nunoya, T. & Ueda, S. (2009). Prevalence of swine Torque teno virus genogroups 1 and 2 in Japanese swine with suspected post-weaning multisystemic wasting syndrome and porcine respiratory disease complex. *Vet Microbiol* 139, 347-50.

Zheng, H., Ye, L., Fang, X., Li, B., Wang, Y., Xiang, X., Kong, L., Wang, 515 ng, W., Zeng, Y., Ye, L., Wu, Z., She, Y. & Zhou, X. (2007). Torque Teno Virus (SANBAN Isolate) ORF2 Protein Suppresses NF-{kappa}B Pathways via Interaction with I{kappa}B Kinases. *J Virol* 81, 11917-11924.

EXAMPLES

Example 1

Quantitative Real Time PCR for the Detection of sTTV Viral DNA.

Equipment Used.

0.2 ml thermo-strip: Thermo Scientific (Westburg)
Hard-Shell 96-Well PCR Plates: Biorad (cat no. HSP-9635)
Microseal 'B' Film: Biorad (cat no. MSB 1001)
IsoFreeze™ PCR chiller rack: IsoFreeze
Heating block: Thermomixer comfort (Eppendorf)
Microcentrifuge: Eppendorf 5418
Centrifuge for microtiter-plates: Eppendorf 5804R
PCR-workstation: Herolab CleneCab
CFX 96 Real-Time System: Biorad Isolation of DNA DNA from 200 µl serum, derived from 5 different pigs was isolated using a QIAamp® MinElute® Virus Spin Kit (Qiagen cat no. 57704). The procedure as described by the manufacturer in the handbook supplied with the kit was applied.

Buffer AVE was used as protease resuspension buffer and the recommended wash step with buffer AW1 was performed. The recommended membrane drying at 56° C. was not performed.

To elute DNA from the column, 50 µl of buffer AVE was used.

PCR-Reaction

Master Mix for 15 Reactions:

187.5 µl iQ™-SYBR® Green Supermix (BioRad, cat no. 170-8882)
82.5 µl Water for injection
15.0 µl 10 µM forward primer: TTVall-F1: CGAATGGCTGAGTTTATGCCGC
15.0 µl 10 µM reverse primer: TTVall-R4: CCTGCCCGATAGGCCCCTTG
300.0 µl To 13 wells of a 96-wells plate was added 20 µl of the master-mix and 5 µl of isolated DNA, plasmid DNA of the standard dilution series or water.

Standard Dilution Series:

The standard dilution series contained 6 samples with a concentration of the plasmid TTV008 (containing a 320 bp-fragment of the 5' UTR of TTSuV-type 2 see addendum 1) of $5 \times 10^5$ copies/µl down to $5 \times 10^0$ copies/µl. Because 5 µl standard was added to each PCR-reaction, the standard dilution curve in the PCR ranged from $2.5 \times 10^6$ copies to $2.5 \times 10^1$ copies of DNA.

PCR-Machine Programming

A CFX 96 Real-Time System (Bio Rad) was programmed as follows:

| Step 1: | 95° C. 5 minutes |
|---|---|
| Step 2: 40 x | 95° C. 30 seconds |
| | 62° C. 15 seconds |
| | 68° C. 30 seconds <=fluorescence is measured |
| Step 3: | 68° C. 7 minutes |
| Step 4: | Meltcurve: 70° C.-95° C., increment 0.5° C./5 sec |

Results

FIG. 1 shows the amplification curve (FIG. 1a) and standard curve (FIG. 1b) chart of the broad spectrum qPCR for porcine TTV. In the amplification chart the grey curves represent the standard dilution series and the black curves represent the samples and no template controls. In the standard curve chart the dots represent the standard dilution series and the crosses represent the samples.

TABLE 1

Data belonging to the amplification and standard curve chart. The starting quantity is the amount of TTSuV particles in the 5 µl DNA isolate, which is put in the PCR.

| Content | Target | Threshold Cycle (Ct) | Starting Quantity (SQ) | Log SQ |
|---|---|---|---|---|
| Std-1 | 2.50E+06 | 17.25 | | 6.398 |
| Std-2 | 2.50E+05 | 21.04 | | 5.398 |
| Std-3 | 2.50E+04 | 24.53 | | 4.398 |
| Std-4 | 2.50E+03 | 27.30 | | 3.398 |
| Std-5 | 2.50E+02 | 30.67 | | 2.398 |
| Std-6 | 2.50E+01 | 34.13 | | 1.398 |
| Unkn-01 | Pig 141 | 34.20 | 2.34E+01 | 1.369 |
| Unkn-02 | Pig 151 | 33.24 | 4.58E+01 | 1.661 |
| Unkn-03 | Pig 161 | 29.06 | 8.34E+02 | 2.921 |
| Unkn-04 | Pig 204 | 25.56 | 9.46E+03 | 3.976 |
| Unkn-05 | Pig 205 | 25.06 | 1.34E+04 | 4.128 |
| NTC | Water | N/A | N/A | N/A |
| NTC | Water | N/A | N/A | N/A |

FIG. 2 shows the melt peaks of the amplicons. The grey curves represent the standard dilution series and the black curves represent the samples. All samples showed one peak with a melting temperature between 85.0° C. and 86.5° C., indicating that the measured fluorescence was derived from only the PCR product.

TABLE 2

Data belonging to the melt peak chart.

| Content | Target | Melt Temp | Peak Height | Begin Temp | End Temp |
|---|---|---|---|---|---|
| Std-1 | 2.50E+06 | 86.5 | 1939.64 | 80.5 | 91.0 |
| Std-2 | 2.50E+05 | 86.5 | 2049.13 | 80.5 | 93.5 |
| Std-3 | 2.50E+04 | 86.5 | 1891.92 | 80.0 | 93.5 |
| Std-4 | 2.50E+03 | 86.5 | 1959.75 | 79.0 | 93.0 |
| Std-5 | 2.50E+02 | 86.5 | 1781.68 | 80.0 | 94.0 |
| Std-6 | 2.50E+01 | 86.5 | 1570.47 | 80.0 | 90.5 |
| Unkn-01 | Pig 141 | 85.5 | 1195.51 | 79.5 | 93.5 |
| Unkn-02 | Pig 151 | 86.0 | 1299.24 | 79.5 | 91.0 |
| Unkn-03 | Pig 161 | 85.5 | 1587.08 | 79.5 | 92.5 |
| Unkn-04 | Pig 204 | 85.0 | 1735.64 | 79.0 | 91.5 |
| Unkn-05 | Pig 205 | 85.5 | 1800.00 | 79.5 | 91.0 |

Conclusion

All 5 samples were shown to be TTV positive. The concentration ranged between $1.34 \times 10^4$ and $2.34 \times 10^1$ copies/reaction, which equals between $6.71 \times 10^5$ and $1.17 \times 10^3$ copies of TTV DNA/ml serum.

Example 2

RT-PCR for the Detection of sTTV Viral mRNA.

Total RNA will be extracted from $2.5 \times 10^5$ porcine kidney (PK) cells. Cells will be disrupted using 600 µl TRIZOL® Reagent (Invitrogen) and 120 µl 1-bromo-3-chloropropane (BCP, Sigma), the suspension will subsequently be centrifuged at 12,000×g at 4° C. for 15 minutes. The aqueous phase will be obtained, precipitated with 300 µl 100% isopropyl alcohol and then centrifuged at 12,000×g at 4° C. for 10 min. The resulting RNA pellet is washed with 1 ml 75% ethanol and dried on air. RNA is subsequently dissolved in RNase-free water. Contaminating DNA is removed from RNA preparations using TURBO DNA-Free™ Kit (Ambion, Applied Biosystems). Briefly, 2 units DNase is added per 10 µg of RNA, incubated at 37° C. for 30 min DNase is inactivated and removed from the RNA sample by centrifugation at 10.000×g for 1.5 min and RNA transferred to a new tube. The RNA will be quantified and the purity will be checked using a Nano-Drop (Thermo Fisher Scientific) spectrophotometer.

Five hundred nanograms of RNA this obtained is converted to complementary DNA (cDNA) using the polydT primer (5'-TTTTTTTTTTTTTTTTTTTTTT$\underline{V}$-3'    (V=A/C/G)) and the SuperScrip™ II Reverse Transcriptase (RT) System (Invitrogen Corporation) according to the manufacturer's protocol. Negative RT control is performed using sterile water instead of Superscript™ II RT. To verify the presence of TTSuVs mRNA, PCRs are performed using the polydT primer and FW1 (5'-CTGGGCGGGTGCCG-3') or FW2 (5'-AGTCAAGGGGCCTATCG$\underline{R}$GC-3'). The amplification products are then run on a 1.8% agarose gel, and PCR products are extracted from gel and sequenced to verify the correct amplification.

---

The invention claimed is:

1. A method for the detection of the presence of replicating sTTV in a sample, characterised in that said method comprises the steps of:
   a) performing a reverse transcriptase polymerase chain reaction (RT-PCR) of said sample using a primer set comprising a forward primer and at least one reverse primer,
      wherein said forward primer binds to a stretch of at least 14 consecutive nucleotides of an oligonucleotide FRNA-a that comprises the nucleotide sequence of SEQ ID NO: 4 or said forward primer binds to a stretch of at least 14 consecutive nucleotides of an oligonucleotide FRNA-b that comprises the nucleotide sequence of SEQ ID NO: 5, and
      wherein said at least one reverse primer binds to a stretch of at least 14 consecutive 5'-terminal nucleotides of an oligonucleotide RRNA-1 that comprises the nucleotide sequence of SEQ ID NO: 6, an oligonucleotide RRNA-2 that comprises the nucleotide sequence of SEQ ID NO: 7 or an oligonucleotide RRNA-3 that comprises the nucleotide sequence of SEQ ID NO: 8, and
   b) examining the RT-PCR amplification result of step (a).

2. A method for the detection of the presence of replicating sTTV according to claim 1, characterised in that said forward primer binds to a stretch of at least 14 consecutive nucleotides of an oligonucleotide FRNA-a that comprises the nucleotide sequence of SEQ ID NO: 4.

3. A method for the detection of the presence of replicating sTTV according to claim 2, characterised in that said method additionally comprises the step of examining the PCR amplification result of step (a) using a probe binding to a stretch of at least 14 consecutive nucleotides of an oligonucleotide that comprises the nucleotide sequence of SEQ ID NO: 5.

4. A method according to claim 1, characterised in that the step of performing the PCR and/or RT-PCR reaction of said method additionally comprises at least one additional non-TTV related primer set and at least one additional non-TTV related template.

5. A method according to claim 1, characterised in that said method comprises an RNA and/or DNA purification step preceding step a).

6. The method of claim 1 wherein said the reverse primer comprises the nucleotide sequence of SEQ ID NO: 6.

7. A method according to claim 6, characterised in that the step of performing the PCR and/or RT-PCR reaction of said method additionally comprises at least one additional non-TTV related primer set and at least one additional non-TTV related template.

8. A method according to claim 6, characterised in that said method comprises an RNA and/or DNA purification step preceding step a).

9. A method for the detection of the presence of replicating sTTV in a sample, characterised in that said method comprises the simultaneous steps of:
   a) performing a polymerase chain reaction (PCR) of said sample using a primer set comprising a forward primer and a reverse primer
      wherein said forward primer binds to a stretch of at least 14 consecutive nucleotides of an oligonucleotide FDNA-TTV that comprises the nucleotide sequence of SEQ ID NO: 1 and
      wherein said reverse primer binds to a stretch of at least 14 consecutive nucleotides of an oligonucleotide RDNA-TTV-r1 that comprises the nucleotide sequence of SEQ ID NO: 2, and
   b) performing a reverse transcriptase polymerase chain reaction (RT-PCR) of said sample using a primer set comprising a forward primer and at least one reverse primer,
      wherein said forward primer binds to a stretch of at least 14 consecutive nucleotides of an oligonucleotide FRNA-b that comprises the nucleotide sequence of SEQ ID NO: 5 and
      wherein said at least one reverse primer binds to a stretch of at least 14 consecutive nucleotides of an oligonucleotide RRNA-1 that comprises the nucleotide sequence of SEQ ID NO: 6, an oligonucleotide RRNA-2 that comprises the nucleotide sequence of SEQ ID NO: 7 or an oligonucleotide RRNA-3 that comprises the nucleotide sequence of SEQ ID NO: 8, and
   c) examining the (RT)-PCR amplification result of steps a) and b).

10. The method according to claim 9, characterised in that the step of performing the PCR and/or RT-PCR reaction of said method additionally comprises at least one additional non-TTV related primer set and at least one additional non-TTV related template.

11. The method according to claim 9, characterised in that said method comprises an RNA and/or DNA purification step preceding step a).

* * * * *

SEQUENCE LISTING

```
<160> NUMBER OF SEQ ID NOS: 9

<210> SEQ ID NO 1
<211> LENGTH: 22
<212> TYPE: DNA
<213> ORGANISM: swine torque teno virus
<220> FEATURE:
<221> NAME/KEY: misc_feature
<222> LOCATION: (2)..(2)
<223> OTHER INFORMATION: s = g or c
<220> FEATURE:
<221> NAME/KEY: misc_feature
<222> LOCATION: (9)..(9)
<223> OTHER INFORMATION: w = a or t/u
<220> FEATURE:
<221> NAME/KEY: misc_feature
<222> LOCATION: (12)..(12)
<223> OTHER INFORMATION: r = g or a
<220> FEATURE:
<221> NAME/KEY: misc_feature
<222> LOCATION: (14)..(14)
<223> OTHER INFORMATION: y = t/u or c
<220> FEATURE:
<221> NAME/KEY: misc_feature
<222> LOCATION: (18)..(18)
<223> OTHER INFORMATION: r = g or a

<400> SEQUENCE: 1
csaatggcwg artytatrcc gc                                              22

<210> SEQ ID NO 2
<211> LENGTH: 17
<212> TYPE: DNA
<213> ORGANISM: swine torque teno virus
<220> FEATURE:
<221> NAME/KEY: misc_feature
<222> LOCATION: (15)..(15)
<223> OTHER INFORMATION: v = a or g or c

<400> SEQUENCE: 2
ctgggcgggt gccgvag                                                    17

<210> SEQ ID NO 3
<211> LENGTH: 26
<212> TYPE: DNA
<213> ORGANISM: swine torque teno virus
<220> FEATURE:
<221> NAME/KEY: misc_feature
```

```
<222> LOCATION: (3)..(3)
<223> OTHER INFORMATION: r = g or a
<220> FEATURE:
<221> NAME/KEY: misc_feature
<222> LOCATION: (6)..(6)
<223> OTHER INFORMATION: y = t/u or c
<220> FEATURE:
<221> NAME/KEY: misc_feature
<222> LOCATION: (13)..(13)
<223> OTHER INFORMATION: r = g or a
<220> FEATURE:
<221> NAME/KEY: misc_feature
<222> LOCATION: (15)..(15)
<223> OTHER INFORMATION: y = t/y or c
<220> FEATURE:
<221> NAME/KEY: misc_feature
<222> LOCATION: (16)..(16)
<223> OTHER INFORMATION: w = a or t/u
<220> FEATURE:
<221> NAME/KEY: misc_feature
<222> LOCATION: (18)..(18)
<223> OTHER INFORMATION: y = t/y or c
<220> FEATURE:
<221> NAME/KEY: misc_feature
<222> LOCATION: (21)..(21)
<223> OTHER INFORMATION: r = g or a
<220> FEATURE:
<221> NAME/KEY: misc_feature
<222> LOCATION: (24)..(24)
<223> OTHER INFORMATION: d = a or g or t/u

<400> SEQUENCE: 3
cgragycaag ggrcywaycg rgcdgg                                    26

<210> SEQ ID NO 4
<211> LENGTH: 28
<212> TYPE: DNA
<213> ORGANISM: swine torque teno virus
<220> FEATURE:
<221> NAME/KEY: misc_feature
<222> LOCATION: (1)..(1)
<223> OTHER INFORMATION: y - t/u or c
<220> FEATURE:
<221> NAME/KEY: misc_feature
<222> LOCATION: (7)..(7)
<223> OTHER INFORMATION: r = g or a
<220> FEATURE:
<221> NAME/KEY: misc_feature
<222> LOCATION: (9)..(9)
<223> OTHER INFORMATION: m = a or c
<220> FEATURE:
<221> NAME/KEY: misc_feature
<222> LOCATION: (11)..(11)
<223> OTHER INFORMATION: m = a or c
<220> FEATURE:
<221> NAME/KEY: misc_feature
<222> LOCATION: (26)..(26)
<223> OTHER INFORMATION: v = a or g or c

<400> SEQUENCE: 4
ygtctarcmg mctgggcggg tgccgvag                                  28

<210> SEQ ID NO 5
<211> LENGTH: 26
<212> TYPE: DNA
<213> ORGANISM: swine torque teno virus
<220> FEATURE:
<221> NAME/KEY: misc_feature
<222> LOCATION: (3)..(3)
<223> OTHER INFORMATION: r = g or a
<220> FEATURE:
<221> NAME/KEY: misc_feature
<222> LOCATION: (6)..(6)
<223> OTHER INFORMATION: y = t/u or c
<220> FEATURE:
```

```
<221> NAME/KEY: misc_feature
<222> LOCATION: (13)..(13)
<223> OTHER INFORMATION: r = g or a
<220> FEATURE:
<221> NAME/KEY: misc_feature
<222> LOCATION: (15)..(15)
<223> OTHER INFORMATION: y = t/u or c
<220> FEATURE:
<221> NAME/KEY: misc_feature
<222> LOCATION: (16)..(16)
<223> OTHER INFORMATION: w = a or t/u
<220> FEATURE:
<221> NAME/KEY: misc_feature
<222> LOCATION: (18)..(18)
<223> OTHER INFORMATION: y = t/y or c
<220> FEATURE:
<221> NAME/KEY: misc_feature
<222> LOCATION: (21)..(21)
<223> OTHER INFORMATION: r = g or a
<220> FEATURE:
<221> NAME/KEY: misc_feature
<222> LOCATION: (24)..(24)
<223> OTHER INFORMATION: d = a or g or t/u

<400> SEQUENCE: 5
cgragycaag ggrcywaycg rgcdgg                                          26

<210> SEQ ID NO 6
<211> LENGTH: 25
<212> TYPE: DNA
<213> ORGANISM: swine torque teno virus

<400> SEQUENCE: 6
taaaaaaaaa aaaaaaaaaa aaaaa                                           25

<210> SEQ ID NO 7
<211> LENGTH: 25
<212> TYPE: DNA
<213> ORGANISM: swine torque teno virus

<400> SEQUENCE: 7
gaaaaaaaaa aaaaaaaaaa aaaaa                                           25

<210> SEQ ID NO 8
<211> LENGTH: 25
<212> TYPE: DNA
<213> ORGANISM: swine torque teno virus

<400> SEQUENCE: 8
caaaaaaaaa aaaaaaaaaa aaaaa                                           25

<210> SEQ ID NO 9
<211> LENGTH: 323
<212> TYPE: DNA
<213> ORGANISM: swine torque teno virus

<400> SEQUENCE: 9
agttacacat aaccaccaaa ccacaggtaa actctgcaaa aaagaggaaa taaatctcat     60
tggttgggcc agaagtcctc attagaatac taaaggacc aatcagaaac acttcctctt    120
ttagagtata taagtaagtg cgcagacgaa tggctgagtt tatgccgctg gtggtagaca   180
cgaacagagc tgagtgtcta accgcctggg cgggtgccgg agctcctgag agcggagtca   240 agggggcctat cggcaggcg gtaatccagc ggaaccgggc cccccctca atggaagaaa    300 gatggctgac ggtagcgtac tgc                                           323
```